United States Patent [19]

Higham et al.

[11] Patent Number: 5,745,366
[45] Date of Patent: Apr. 28, 1998

[54] PHARMACEUTICAL DISPENSING DEVICE AND METHODS

[75] Inventors: John D. Higham, Menlo Park; Peter P. Godlewski, San Carlos; Richard C. Arnold, San Jose, all of Calif.

[73] Assignee: Omnicell Technologies, Inc., Palo Alto, Calif.

[21] Appl. No.: 544,379

[22] Filed: Oct. 10, 1995

Related U.S. Application Data

[63] Continuation-in-part of Ser. No. 274,926, Jul. 14, 1994.

[51] Int. Cl.$^6$ .............................. G06F 17/00; G06G 7/48
[52] U.S. Cl. .............................. 364/479.12; 364/479.1; 364/479.11; 364/479.14; 312/215
[58] Field of Search ........................ 364/479, 900, 364/403; 361/727, 391; 395/250, 210; 312/215; 221/2, 153; 53/55; 340/825.35

[56] References Cited

U.S. PATENT DOCUMENTS

| | | | |
|---|---|---|---|
| 3,556,342 | 1/1971 | Guarr. | |
| 3,715,148 | 2/1973 | Beals. | |
| 3,744,867 | 7/1973 | Shaw. | |
| 3,917,045 | 11/1975 | Williams et al.. | |
| 4,019,793 | 4/1977 | Gerding. | |
| 4,179,724 | 12/1979 | Bonhomme | 361/391 |
| 4,209,211 | 6/1980 | Alford. | |
| 4,267,942 | 5/1981 | Wick, Jr. et al.. | |
| 4,360,125 | 11/1982 | Martindale et al.. | |
| 4,473,884 | 9/1984 | Behl. | |
| 4,635,053 | 1/1987 | Banks et al. | 340/825.31 |
| 4,695,954 | 9/1987 | Rose et al.. | |
| 4,737,910 | 4/1988 | Kimbrow | 364/403 |
| 4,783,740 | 11/1988 | Ishizawa et al. | 364/403 |
| 4,785,969 | 11/1988 | McLaughlin. | |
| 4,811,764 | 3/1989 | McLaughlin. | |
| 4,847,764 | 7/1989 | Halvorson. | |
| 4,866,661 | 9/1989 | De Prins | 364/900 |
| 4,942,275 | 7/1990 | Addey et al.. | |
| 4,962,491 | 10/1990 | Schaeffer. | |
| 4,967,928 | 11/1990 | Carter. | |
| 5,014,875 | 5/1991 | McLaughlin et al. | 221/2 |
| 5,047,948 | 9/1991 | Turner. | |
| 5,055,660 | 10/1991 | Bertagna et al.. | |
| 5,069,511 | 12/1991 | Swets et al.. | |
| 5,259,668 | 11/1993 | Teufel et al.. | |
| 5,263,596 | 11/1993 | Williams | 221/153 |
| 5,267,174 | 11/1993 | Kaufman et al.. | |
| 5,276,810 | 1/1994 | Kitamura et al. | 395/250 |
| 5,291,191 | 3/1994 | Moore | 340/825.35 |
| 5,314,243 | 5/1994 | McDonald et al. | 312/215 |
| 5,346,297 | 9/1994 | Colson, Jr. et al. | 312/215 |
| 5,381,315 | 1/1995 | Hamaguchi et al. | 361/727 |
| 5,460,294 | 10/1995 | Williams | 221/2 |
| 5,502,944 | 4/1996 | Kraft et al. | 53/55 |
| 5,537,313 | 7/1996 | Pirelli | 364/403 |
| 5,564,803 | 10/1996 | McDOnald et al. | 312/215 |
| 5,611,051 | 3/1997 | Pirelli | 395/210 |

*Primary Examiner*—Reba I. Elmore
*Assistant Examiner*—Monica Lewis
*Attorney, Agent, or Firm*—Townsend and Townsend and Crew LLP

[57] ABSTRACT

The invention provides improved methods and apparatus for providing access to items to be dispensed and for maintaining an inventory of the items. According to one aspect of the invention, a dispensing unit is provided having an enclosure with an interior. A plurality of storage locations are distributed over a surface of the enclosure. Sensors associated with at least some of the individual storage locations are provided. The unit further includes a multiplicity of receptacles disposed within at least some of the storage locations. Sensors associated with at least some of the individual receptacles are provided. A processor is disposed on the enclosure and connected to receive signals from the storage location-associated sensors and the receptacle-associated sensors.

43 Claims, 29 Drawing Sheets

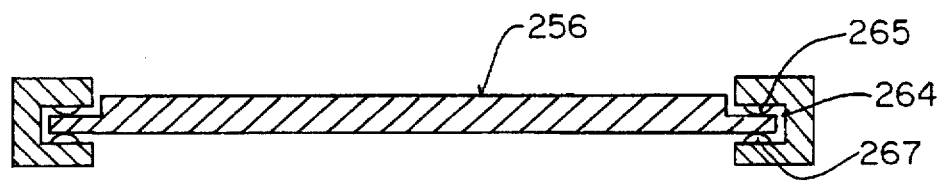
FIG. 23
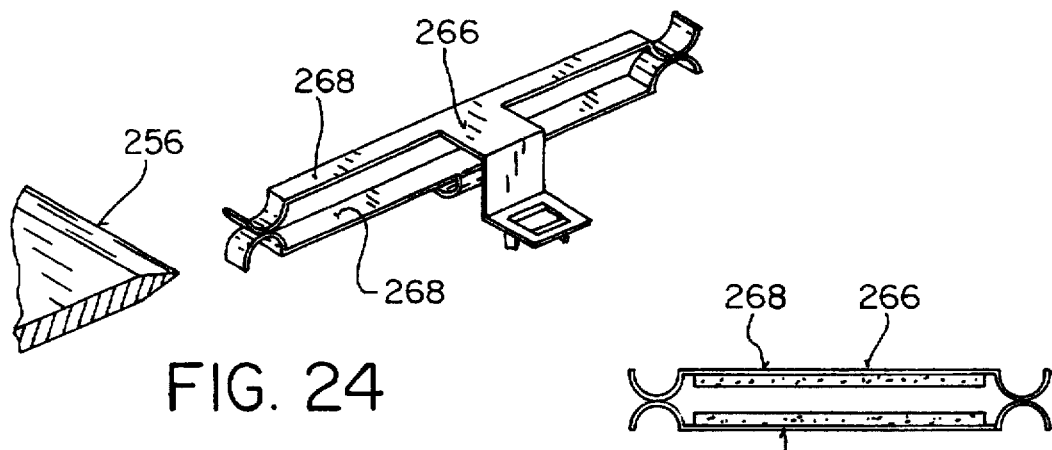
FIG. 24
FIG. 25
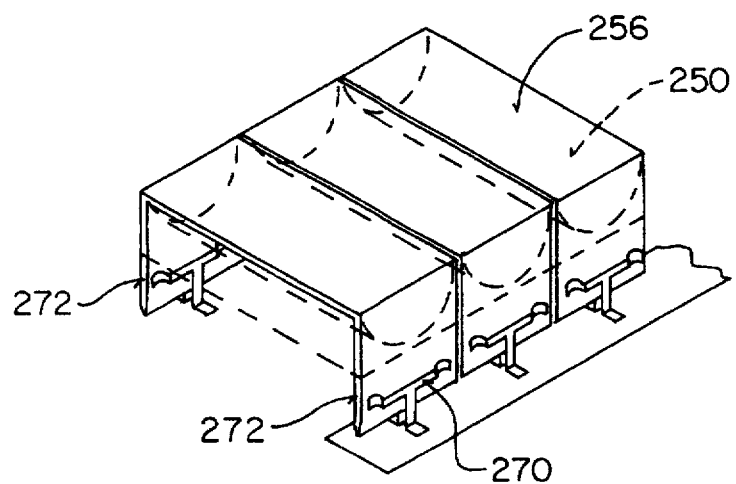
FIG. 26

PHARMACEUTICAL DISPENSING DEVICE AND METHODS

CROSS-REFERENCE TO RELATED APPLICATIONS

This application is a continuation-in-part application of U.S. patent application Ser. No. 08/274,926, filed Jul. 14, 1994, the disclosure of which is herein incorporated by reference.

BACKGROUND OF THE INVENTION

1. Field of the Invention

The invention relates to methods and apparatus for providing access to items to be dispensed, and may find a particular use in the dispensing of medical supplies. The invention further relates maintaining an inventory of the number and type of items dispensed while providing easy and convenient access to the items.

In large medical facilities, inventories of medical supplies are held in storage locations which are often far removed from the patients who use them. To facilitate delivery of the medical supplies from the storage area to the patient, a variety of dispensing systems have been proposed. In one such system, referred to as a "cart exchange" system, dispensing carts are distributed at remote dispensing stations in the medical facility and are periodically exchanged with fully supplied carts. The "used" cart is returned to a central supply area where inventory decreases of particular medical supplies are recorded and the cart is restocked to predetermined "par" levels. These par levels are intended to ensure constant availability of required medical supplies.

In a similar system, individual carts are used but are not removed from their remote locations in the medical facility. Instead, a larger cart holding a variety of medical supplies is circulated throughout the facility to restock individual carts to their par levels.

Although these systems are generally effective in providing medical supplies to remote locations away from the storage area, they suffer from a number of drawbacks. One particular drawback is the potential for stock-outs that can arise if the inventories of the carts are not closely monitored. Adequate inventory monitoring can be problematic due to time limitations on the hospital staff. Depletion of certain items from the carts can pose serious risks to the patients in the medical facility.

To ensure that sufficient supplies are maintained in the carts, overstocking can occur which in turn increases the cost of the medical facility's inventory system by requiring more items to be maintained in inventory than are actually required. Excessive restocking is also demanding on the hospital staff who must devote more of their time to monitoring the carts to ensure that sufficient supplies are available.

Another drawback of the above-described inventory systems is the lack of security provided for the supplies maintained on the carts. Since access to the items can usually be gained without recording user identification information, medical personal may neglect or forget to record removal of the accessed supplies which can introduce errors or inefficiencies into the medical facility's inventory system. Lack of security can also discourage the return of unused supplies. Without a record of user access and removal, medical personnel may often choose to discard the supplies rather than taking the time to return them.

In yet another drawback, no direct data transfer from the supply carts to the hospital inventory and billing systems is provided. This can lead to further inefficiencies in the inventory system.

For these and other reasons, it would be desirable to provide a dispensing system allowing easy and convenient access to the items to be dispensed while also maintaining an accurate inventory (including both removal and replacement) of the number and type of items to be dispensed. Such a system should reduce the possibility of stock outs and provide accountability by controlling access to the supplies and allowing easy return of unused items. The system should also allow for inventories to be maintained at minimum levels and should be able to directly supply inventory information to the medical facility's inventory and billing systems.

2. Description of the Background Art

U.S. Pat. No. 5,263,596 describes a subassembly for use in a medical dispenser station which dispenses pharmaceutical items in single quantities from a locked storage location.

U.S. Pat. No. 3,715,148 describes a medicine dispensing cabinet having a plurality of sliding drawers and a plurality of dispensing trays.

U.S. Pat. No. 3,556,342 describes a medicine dispensing apparatus for dispensing medicines from a cabinet and into a hopper.

U.S. Pat. No. 5,047,948 describes a medication dispensing system for dispensing medicines into a receptacle in the bottom of a medicine cabinet.

U.S. Pat. No. 4,962,491 describes a portable medication dispenser for visually and audibly indicating the times at which a patient's medications are to be taken.

U.S. Pat. No. 5,014,875 describes a medication dispenser having a housing with a plurality of locked drawers which are stocked with selected pharmaceutical items. Access to the items is allowed upon keyboard entry of a predetermined access code.

U.S. Pat. No. 3,917,045 describes a drug dispensing apparatus for automatically dispensing one or more individual drug doses to a common collection area as required by a patient.

U.S. Pat. No. 4,019,793 describes a pharmaceutical dosage distribution apparatus having an enclosure with a door and a plurality of trays.

U.S. Pat. No. 4,267,942 describes a pharmaceutical storage and dispensing cabinet for dispensing items into a retrieval tray for removal.

U.S. Pat. No. 4,360,125 describes a medication dispenser which can provide a medication alert signal in accordance with a desired medication regimen.

U.S. Pat. No. 4,473,884 describes a portable medical dispensing unit for storing pills. The dispensing unit is programmed with a medication schedule which causes visual and audio signals when it is time for medication to be consumed.

U.S. Pat. No. 4,635,053 describes an apparatus for monitoring and restricting access to individual items which are provided with a unique identifying code. The codes are scanned by a microprocessor to identify removal of the item.

U.S. Pat. No. 4,695,954 describes a system and method for dispensing medications prescribed by a doctor. The system includes a medical dispenser which can read prescription information from a memory device and make the medications available to the patient at the prescribed times.

U.S. Pat. No. 4,783,740 describes an inventory management system having a central control unit and a number of parts terminal units that are disposed at each parts container.

U.S. Pat. No. 4,785,969 describes a medication dispensing system for controlled programmed dispensing of medication to a patient and for creating a retrievable patient medication record.

U.S. Pat. No. 4,811,764 describes a medication dispenser station having rotatable carousels with vertically open compartments containing individual doses of a medication.

U.S. Pat. No. 4,847,764 describes a system for dispensing medications in a health care institution.

U.S. Pat. No. 4,942,275 describes a control panel face for mounting to a control member.

U.S. Pat. No. 4,967,928 describes a medication cart for dispensing medicines during a nurse's rounds.

U.S. Pat. No. 5,055,660 describes a transaction monitoring and security system for recording data from the sale of articles.

U.S. Pat. No. 5,069,511 describes a pharmaceutical cart for retaining a plurality of dispensing bins on shelves.

U.S. Pat. No. 5,259,668 describes a medication cart having a base formed of a pair of molded plates interconnected by rails. The plates have molded grooves and holes for receiving structural elements of the cart.

U.S. Pat. No. 5,267,174 describes a medication delivery device having a housing containing separate storage locations for holding medication dosages away from access by the user.

SUMMARY OF THE INVENTION

The invention provides a dispensing unit having an enclosure with an interior. A plurality of storage locations are distributed over a surface of the enclosure. Sensors are associated with at least some of the individual storage locations to sense when the storage locations have been accessed. A multiplicity of receptacles are disposed within at least some of the storage locations, and sensors are associated with at least some of the individual receptacles to sense when an item has been removed (or in some cases returned) from the receptacles. A processor is disposed on the enclosure and connected to receive signals from the storage location-associated sensors and the receptacles-associated sensors.

In an exemplary embodiment, at least one of the storage locations comprises a drawer that can be withdrawn from the interior of the enclosure. The drawer preferably includes at least one divider to divide the drawer into the multiplicity of receptacles. In an exemplary aspect of this embodiment, the storage-location sensors comprise a switch disposed near each drawer for sensing when a drawer has been opened. When the drawer is withdrawn from the interior, the switch sends a signal to the processor indicating that this drawer has been accessed. In another exemplary aspect, the receptacle-associated sensors comprise touch-sensitive buttons. Preferably, the buttons are disposed in a row on the surface of the enclosure and in an order which corresponds to the order of receptacles in the drawer.

In one particular aspect, a signal received from a switch when one of the drawers is opened is used by the processor to set the row of buttons to correspond to the receptacles in the accessed drawer. This configuration allows one row of buttons to be used with more than one drawer, and reduces the number of buttons required for the unit.

In another particular aspect, each button is assigned a unique button identification symbol, e.g., a number. The identification symbol is disposed in close proximity to each of the buttons. The same button identification symbols are also disposed in close proximity to each of the receptacles. With this configuration, when one of the drawers is opened and one of the buttons is selected, removal (or replacement) of an item from the receptacle having the same identification symbol as the button is recorded.

In yet another particular aspect, each drawer includes a unique drawer identification symbol that corresponds to the unique button identification symbols. Associating the drawers with the buttons in this manner is advantageous when providing the unit with means for displaying a list of items held by the unit, means for entering a selection from the list of the items held in the dispensing unit into the processor, and a plurality of visual indicators connected to the processor and in close proximity to the buttons. With such a configuration, when a selection from the list of items is entered, the visual indicator in close proximity to the button having the same identification symbol as the drawer containing the item is actuated. This allows a user to easily identify which drawer contains the selected item. In a further aspect, when the drawer having the item is accessed, the visual indicator in close proximity to the button having the same identification symbol as the receptacle having the item is actuated. This allows for easy identification of the receptacle having the item.

In another exemplary aspect, the unit is provided with a horizontal shelf having the buttons disposed thereon. The drawers are slidably disposed along the shelf and are generally aligned with the buttons such that each button corresponds to the closest drawer. Means are provided for displaying a list of items held by the unit for entering a selection from the list of the items held in the dispensing unit into the processor. A plurality of visual indicators connected to the processor and in close proximity to the buttons are provided, with each button corresponding to the closest visual indicator. With this configuration, entry of a selection from the list of names actuates the visual indicator corresponding to the drawer having the item. This allows for easy identification of the drawer having the desired item. Once the drawer having the item is accessed, the visual indicator corresponding to the button having the same symbol as the receptacle having the item is actuated. This allows for easy identification of the receptacle having the item once the drawer is opened.

In another exemplary embodiment, at least one of the storage locations comprises a rack having a plurality of pegs. The pegs are disposed along the rack to define the receptacles. In an exemplary aspect, the storage-location sensors comprise a switch disposed near each rack for sensing the opening of the racks. In another aspect, the receptacle-associated sensors comprise touch-sensitive buttons. Preferably, the buttons are disposed in a row on the surface of the enclosure.

In one particular exemplary aspect, the signal received from one of the switches when one of the racks is open is used by the processor to set the row of buttons to correspond to the pegs in the accessed rack. This configuration allows a single row of buttons to be used with more than one rack. Each time a rack is accessed, the buttons are set to correspond to that particular rack.

In another particular aspect, the buttons correspond visually with the pegs by a unique button identification symbol in close proximity in corresponding to each button and each peg. When a rack is withdrawn and one of the buttons is selected, removal (or replacement) of an item from the peg having the same identification symbol as the button is recorded.

In yet another particular aspect, the unit further includes a horizontal shelf with the buttons being disposed along the shelf. The racks are slidably disposed along the shelf and generally aligned with the buttons such that each button corresponds to the closest rack. Means are provided for displaying a list of items held by the unit, and means for entering a selection from the list of the items held in the dispensing unit into the processor are provided. A plurality of visual indicators connected to the processor and in close proximity to the buttons are provided, with each button corresponding to the closest visual indicator. With this configuration, entry of a selection from the list of items actuates the visual indicator corresponding to the rack having the item. This allows for easy visual identification of the rack having the desired item. When the rack having the item has been accessed, the visual indicator corresponding to the button having the same identification symbol as the peg having the item is actuated. This provides for easy visual identification of the peg having the desired item once the rack has been withdrawn. As each item is withdrawn, the associated button is pushed once to record removal.

In still another aspect, the unit further includes means for selectively preventing access to the storage locations. Means are also provided for opening the preventing means to permit access to a desired receptacle in response to input of patient and user identification information into the processor. In one aspect, the storage locations comprise a plurality of racks, and withdrawal of one of the racks causes the preventing means to block access to all remaining racks. In another aspect, the storage locations comprise a plurality of drawers, and withdrawal of one of the drawers causes the preventing means to block access to all remaining drawers.

In another particular aspect, the interior is accessible through a doorway, and means are provided across the doorway for selectively blocking access to the storage locations while permitting access to the receptacle-associated sensors at all times. Means for opening the blocking means are provided to permit access to a desired receptacle selected from the plurality of receptacles in response to actuation of the receptacle-associated sensor is provided.

The invention further provides a dispensing unit comprising an enclosure having an interior. A plurality of pull-out compartments on the enclosure are provided with at least some of the compartments being provided with an array of receptacles. A sensor is associated with and in close proximity to each of the receptacles for sensing when an item has been removed from one of the receptacles. A processor is disposed on the enclosure and connected to receive signals from the sensors. In a preferred aspect, the compartments comprise drawers having dividers to form the receptacles, and the sensors comprise touch-sensitive buttons disposed on the drawers.

In one particular aspect, the dividers are adjustable so that the number and size of the receptacles can be varied. Sensor covers are provided to prevent access to selected sensors based on the adjustment of the dividers so that each receptacle will have only one accessible button.

In a particular preferred aspect, a visual indicator is disposed in close proximity to each sensor. In another aspect, means are provided for displaying a list of items held in the unit and for entering a selection from the list of the items held in the dispensing unit into the processor. With this configuration, entry of a selection from the list of items actuates the visual indicator in close proximity to the receptacle having the selected item. This allows for convenient identification of a particular receptacle having the item.

In another particular aspect, a cover is provided for each of the receptacles. The covers are preferably connected to the dividers by hinges so that the receptacles can be accessed by lifting an edge of the covers. In another aspect, the covers are preferably substantially transparent to allow visual access to the receptacles. Sensing means are provided for sensing when the covers have been displaced. In one aspect, the sensing means comprises an electromagnetic sensor or an optical sensor. When one of the covers is lifted, a signal is sent to the processor to produce a record of the access. This information can then be used to determine which users have been accessing the receptacles.

In another aspect, locks are provided for locking the cover to the receptacles to prevent access to the receptacles. The locks are in communication with the processor which provides signals to lock or unlock the covers. Preferably, the processor sends a signal to unlock one of the covers after both user, patient, and item identification information have been entered into the processor.

In still another particular aspect, the buttons are disposed beneath the covers and an aperture is disposed in each of the covers with the aperture being aligned with the button. With this configuration, the buttons can be accessed through the apertures while the covers are closed. Once a button has been actuated, the cover is unlocked to allow access to that particular receptacle. This configuration provides security to the dispensing unit by ensuring that access to a particular receptacle will not be obtained until the associated button has been selected to record removal of an item.

In another aspect of the dispensing unit, at least some of the compartments comprise racks with the receptacles being disposed along pegs on the racks. The sensors are disposed along the racks and near each peg. In one particular embodiment, the sensors are disposed on the pegs for sensing when an item has been removed from the associated peg. This embodiment allows an item to be removed from a peg and to have the removal automatically recorded. In another embodiment, the sensors comprise touch-sensitive buttons. With this embodiment, once an item has been removed (or replaced) from the peg, the associated button is touched to record removal of the item.

In a preferable aspect, a visual indicator in close proximity to each button is provided. Means are provided for displaying a list of items held by the unit and for entering a selection from the list of the items held in the dispensing unit into the processor. Entry of a selection from the list of the items actuates the visual indicator in close proximity to the button having the selected item. This allows for easy visual identification of the peg having the desired item.

In yet another aspect, the sensor is an optical sensor disposed along a side of the drawer. When a user's hand is inserted into the drawer, the optical sensor detects that one of the receptacles has been accessed.

The invention provides a method for recording inventory information related to removal and addition of items from an enclosure. According to the method, a first sensor on the enclosure is actuated to produce a first signal associated with the location of a receptacle. A second sensor on the enclosure is actuated to produce a second signal associated with the location of the receptacle. An item is transferred to or from the receptacle, and the transfer is recorded based on an address of the location which is based at least in part on the first and second signals.

In an exemplary aspect, the first sensor is actuated by withdrawing a drawer or rack holding the item at least partially from the enclosure or by touching a button associated with the drawer or rack holding the item. In another aspect, the second sensor is actuated by touching a button corresponding to the location of the item on the drawer or rack or by removing the item.

In another aspect, the item to be removed or added is selected from a list of items, and selection of the item from the list actuates a visual indicator in close proximity to the drawer or rack having the item. This indicates which drawer or rack has the item. In another aspect, a visual indicator in close proximity to the button which corresponds to the location of the item in the drawer or on the rack is actuated after the drawer or rack has been withdrawn. This indicates the location of the item in the drawer or on the rack.

In yet another aspect, a unique button identification symbol is provided for each button. The symbols are disposed in close proximity to each button and also near each item location. The button is actuated after visually locating both the button identification symbol near the item to be dispensed and the button having the same identification symbol.

In still another aspect, access to the items is prevented until patient identification information has been entered into the dispensing unit.

The invention provides a method for recording inventory information related to removal and addition of items from an enclosure having an array of receptacles disposed in a holding apparatus. According to the method, the holding apparatus is at least partially withdrawn from the enclosure to gain access to the items. An item to be removed or added is visually located and is then removed or added. A sensor in close proximity and corresponding to the receptacle having the item is actuated to record removal or addition of the item, preferably by touching a touch-sensitive button.

In one particular aspect, access to one of the receptacles is sensed (independently of sensing the addition or removal of an item) and a record of the access is produced. The record of receptacle access can then be compared with the record of item removal, and the record of the item removal can then be updated based on the record of receptacle access. In still another aspect, access to the receptacles is prevented until both user and patient identification information have been recorded. In another aspect, access to the receptacles is prevented until actuation of one of the sensors. In another aspect, access to a selected number of the receptacles is prevented based on the user identification information. This provides heightened security by ensuring that only selected individuals can gain access to particular items.

The invention provides an exemplary method for dispensing items from a dispensing unit so that a nurse or other user will be afforded access only to items in the dispensing unit for which the nurse is authorized to access. The dispensing unit preferably includes a plurality of retractable drawers, with at least some of the drawers having a plurality of receptacles for holding the items. According to the method, nurse and item identification information are entered into the dispensing unit. Optionally, patient identification information may also be input or may be selected from a list of patients stored in the dispensing unit. The nurse identification information is then compared with an access list to determine which of the drawers the nurse may be given access. If the nurse may be afforded access to drawers having the requested items, a first one of the drawers is unlocked. All other drawers will preferably remain locked. Optionally, a drawer visual indicator will be actuated to assist the nurse in locating the unlocked drawer.

The unlocked drawer is then retracted to expose the receptacles. A receptacle visual indicator adjacent one of the receptacles having a requested item is actuated to assist the nurse in locating the requested item. Once the item is located, the item is removed from the receptacle. Since the item identification information was previously input into the dispensing unit, the dispensing unit will have a record of the removed item. Optionally, quantity identification information may also be input into the dispensing unit prior to item removal to produce a record of the number of items removed. The lid will preferably be locked until user and item identification information are entered. Then, upon actuation of the adjacent visual indicator, the lid will unlock. After item (or items) is taken from the first receptacle, a visual indicator adjacent another receptacle will be lighted if there are more items to be removed from the retracted drawer. If there are no more items to be dispensed from the retracted drawer, no visual indicators will be actuated and the drawer may be closed. Preferably, the drawer will lock when closed. If there are items to be removed from another drawer, that drawer will unlock and a visual indicator adjacent the next receptacle having an item to be removed will be actuated. This process is repeated until all items from the initially entered item identification information have been dispensed.

In some cases, a single receptacle will not have a sufficient inventory of items (e.g. the receptacle may be too small to hold a large number of items, or the receptacle may not be sufficiently stocked). In such a case, other receptacles may be filled with items of the same type (i.e. the drawer will have multiple bins which are each filled with multiple items of the same type). When a nurse has emptied one of the receptacles, a visual indicator adjacent another receptacle having the same type of item will be actuated. In this way, a pre-entered request for items of the same type may be easily filled even if a single receptacle does not have a sufficient inventory to fill the request. Preferably, the visual indicator adjacent the second receptacle will not be actuated until a lid over the first receptacle is lifted and a corresponding item button is touched or the lifting of the lid is sensed.

In one aspect, the drawer will be configured to have heightened security for the items held therein, and access will be allowed to only the receptacle (or receptacles) in the retracted drawer having the requested item (or items). In the event that access to another receptacle is attempted, an alarm will be produced.

In another aspect, access may be afforded to any receptacle of a retracted drawer. However, if a receptacle is accessed for which an adjacent visual indicator is not actuated, an alarm will be produced. Alternatively, instead of producing an alarm, the nurse can optionally be prompted to enter item identification information into the dispensing unit for additional items that were not originally selected.

In another aspect of the method, the removing step comprises at least partially removing a lid covering the receptacle and sensing removal of the lid. Since item identification information has been pre-entered into the dispensing unit, the sensing of lid removal may then be used to produce a record of item removal, i.e. the sensing of lid removal will serve to confirm that the pre-selected item (or items) has actually been removed. As a reminder to close the lid to prevent further access, an alarm will be produced if the lid is not closed following removal of the item. In yet another aspect, witness identification information will be required to be entered into the dispensing units prior to allowing access to certain drawers having items with restricted access. If no lid is provided, each receptacle may alternatively be provided with an item button which may be touched (usually only once) to confirm item removal and the associated quantity.

In still a further aspect, any emptied receptacles will periodically be restocked. For the drawer with heightened security, access to only one receptacle at a time will be allowed as the receptacles are refilled. Alternatively, the invention provides for the rapid refilling of the emptied receptacles by providing simultaneous access to all of the receptacles in the drawer. In another aspect of the restocking procedure, a list of items and associated quantities that are to be restocked may be entered into the dispensing unit prior to restocking. Usually, restock quantities are input electronically into the dispensing unit from a central computer which is in communication with various dispensing units located within the health care facility and maintains an inventory of items held in each dispensing unit. Further, the drawer may optionally be provided with a touch-sensitive buttons adjacent each receptacle so that the restock person may confirm that the receptacle has been restocked with items corresponding to the pre-entered information. If the restock person wishes to restock an item or a quantity that is different from the pre-entered information, such information may be manually entered into the dispensing unit during the restocking process.

The invention further provides a method for dispensing items from a dispensing unit having a plurality of storage locations, with at least some of the storage locations having a plurality receptacles for holding the items. The method is particularly well suited for dispensing items which do not need to be stored under heightened security. According to the method, nurse identification information, item identification information, and item quantity information are entered into the dispensing unit. A receptacle visual indicator which is adjacent one of the receptacles having an item (or items) from the entered item identification information is then actuated to assist the nurse in locating the item. A touch-sensitive button adjacent the receptacle having the actuated visual indicator is touched to confirm access to that receptacle. Touching of the button may also serve to confirm the pre-entered quantity has been removed. The item is then removed from the receptacle adjacent the actuated visual indicator.

After the item (or items) has been removed from the first receptacle, a second receptacle visual indicator adjacent a second receptacle having another item from the entered item identification information will be actuated. In this way, the nurse will be directed to the next receptacle so that items may continue to be dispensed. In one aspect of the method, an alarm is produced if a touch-sensitive button is pushed for a receptacle other than the receptacle having the actuated visual indicator.

The invention provides a method for returning a previously dispensed item to a dispensing unit. Such a method is provided to maintain an accounting of items that are dispensed and for some reason are not delivered to the patient (e.g. if the wrong item was dispensed or if the item was contaminated after removal). According to the method, nurse (and preferably also patient) identification information are entered into the dispensing unit. Item identification information for the item to be returned is also entered into the dispensing unit. The entered item identification information is then compared with a list of items requiring the presence of a witness when returning the item. If a witness is required, a request for witness identification information to be entered into the dispensing unit is provided. The item is then placed into the dispensing unit.

In one particular aspect, a request for an explanation of why the item is being returned is produced. In another aspect, a request for the quantity of the item being returned is produced. In still a further aspect, the placing step comprises inserting the item into a receptacle having a one-way door. In a preferable aspect, a record of returned items will be produced. Periodically, the returned items will be removed from the dispensing unit and compared to the record of returned items to determine any discrepancies between the record of returned items and the items actually returned.

The invention provides a method for recording inventory information related to removal and addition of items to or from an enclosure having at least one retractable drawer. The drawer includes a plurality of receptacles which are sized to each hold only a single item. According to the method, nurse and item identification information are entered into the dispensing unit. The nurse identification information is compared with an access list to determine whether the nurse may be given access to the drawer. If access may be afforded, the drawer is at least partially retracted from the enclosure to gain access to at least one of the receptacles. A lid from the accessed receptacle is then at least partially removed and its removal is sensed. The item is then withdrawn from the receptacle and a record of the item's removal is produced.

In one aspect, the record is produced at least in part by sensing removal of the lid. Alternatively, the record may be produced by touching an item button in close proximity to the receptacle of the withdrawn item. In this way, a record of the sensed lid removal may be compared with the record of item removal. In a further aspect, the step of removing the lid comprises sliding the lid from the receptacle to provide access to the item. Alternatively, the lid may be lifted from the receptacle to provide access to the item. In still a further aspect, items are periodically restocked into emptied receptacles. In a preferable aspect, the restocking step comprises simultaneously removing all lids from the drawer to gain access to the receptacles.

The invention provides an exemplary dispensing unit, particularly useful in the dispensing of pharmaceutical items in single unit doses. The dispensing unit includes an enclosure having an interior and at least one drawer. A processor is provided for receiving user and item identification information. The drawer includes a plurality of receptacles, with each receptacle being sized to hold a single item. A visual indicator is provided for each receptacle (or for an array of the receptacles), with the visual indicators being in close proximity and corresponding to each receptacle or array of receptacles. A blocking means is provided for the drawer and for each receptacle. Such blocking means are provided for selectively preventing access to the drawer and to each of the receptacles. The processor is in communication with the drawer and the receptacle blocking means and is configured to send a signal to unlock the drawer or receptacle blocking means based on the user and/or item identification information. In this way, the user may be afforded access to selected drawers and receptacles based on the entered identification information. For example, the processor can be employed to limit access to selected drawers based on the user identification information. Further, access to selected receptacles within the drawers can be limited to those having items from the entered item identification information. The dispensing unit further includes a sensing means for sensing access to the receptacles.

The processor is preferably in communication with the sensing means so that a record of removal may be recorded each time a lid is removed. Optionally, a touch sensitive button may be provided for each receptacle so that recordation may occur by touching the button. In some cases, the touch-sensitive button and the visual indicator may be incorporated into a single button.

In one preferable aspect, the receptacle blocking means comprises a plurality of lids, with a separate lid being disposed over each receptacle. In one aspect, at least some of the lids are transparent. To provide additional security to the items in the drawers, at least some of the lids may be opaque to prevent visual access to the items. In one particular aspect, the sensing means comprises a sensor associated with each lid for detecting at least partial removal of each lid from its associated receptacle. With such a configuration, transfer of an item may be recorded by the associated touch-sensitive button while access to each receptacle is recorded upon removal of the lid. In this way, the removal record and the access record may later be compared to determine any discrepancies.

In one particular aspect, the receptacles comprise bins having lids that are slidably held over each of the receptacles. Alternatively, the lids may be attached over each of the receptacles by a hinge. In another aspect, the receptacle comprises a groove formed in a rotatable cylinder. The cylinder is covered by a lid and preferably includes a plurality of grooves so that more than one item may be held beneath a single lid. The cylinder may then be rotated each time the lid is opened so that a single item is available for removal upon each request.

In another aspect, the sensor comprises an electrical circuit, and the lid includes an electrically conductive element for closing the circuit upon removal of the lid. Alternatively, the sensor comprises a photodetector and a light source. In still a further aspect, at least one drawer includes a waste compartment for receiving returned items. The waste compartment preferably includes a one-way door for inserting the items to be returned. In yet a further aspect, a touch sensitive button disposed on the drawer for requesting access to the drawer.

The invention provides an exemplary drawer for a dispensing unit. The drawer is particularly useful in holding single doses of pharmaceutical items and includes a plurality of receptacles, with each receptacle being sized to hold a single item. A plurality of lids are provided for covering at least some of the receptacles. A plurality of touch-sensitive item buttons are provided, with the item buttons being in close proximity to and corresponding to selected ones of the receptacles. A means are provided for simultaneously removing all of the lids to gain access to the receptacles. In a preferable aspect, the drawer further includes a touch-sensitive drawer button for requesting access to the drawer.

BRIEF DESCRIPTION OF THE DRAWINGS

FIG. 23 is a cross-sectional view of a lid of the drawer of the FIG. 19 having an optical sensor according to the present invention.

FIG. 24 is a perspective view of an alternative sensor for the lids of the drawer of FIG. 19.

FIG. 25 is a cross-sectional side view of the sensor of FIG. 24.

FIG. 26 is a perspective view of a further alternative embodiment for the lids and sensors of the drawer of FIG. 19 according to the present invention.

DETAILED DESCRIPTION OF THE SPECIFIC EMBODIMENTS

The invention provides improved methods and apparatus for adding and removing items to or from a dispensing unit and for maintaining an inventory of the items. The methods and apparatus of the invention are particularly useful with the dispensing unit as described generally in U.S. patent application Ser. No. 08/095,619, filed Jul. 21, 1993 (Attorney Docket No. 16166-1), the disclosure of which is herein incorporated by reference. Such a unit allows a user to visually locate an item to be removed and to record removal of the item by pressing a touch-sensitive button in close proximity to the storage location of the item. A similar procedure is used when placing items into the unit.

Figure 1:
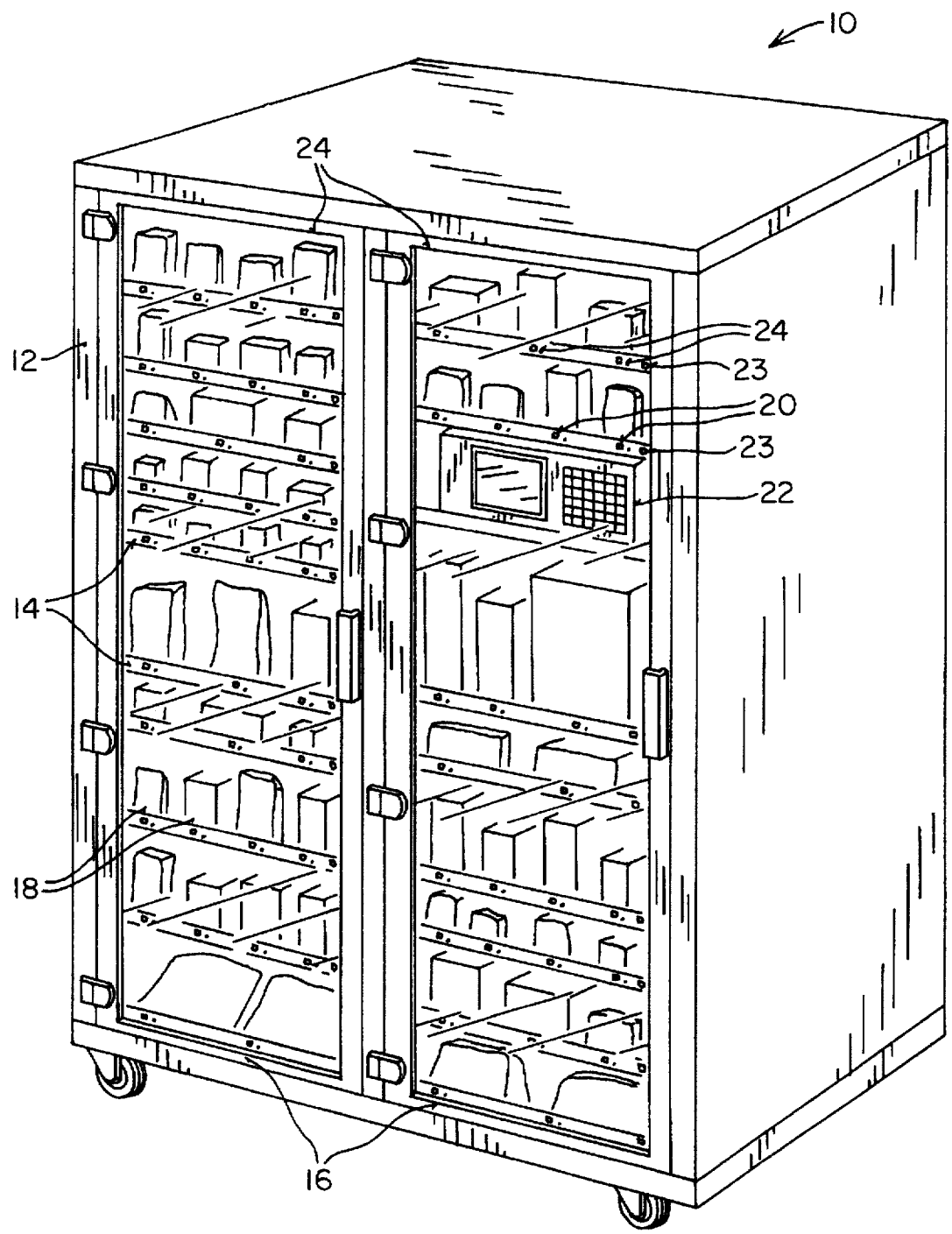
FIG. 1 illustrates a dispensing unit having a plurality of touch-sensitive buttons and corresponding visual indicators for recording inventory information.

An exemplary dispensing unit of the type just described is shown in FIG. 1. Briefly, the dispensing unit 10 includes an enclosure 12 and a plurality of adjustable shelves 14. Optionally, the enclosure 12 can be divided into a plurality of compartments 16 to increase the number of shelves 14 that can be disposed in the enclosure 12. Each shelf 14 can be further subdivided to form a plurality of storage locations 18. Disposed on the shelves 14 and near each storage location 18 are touch-sensitive buttons 20. The buttons 20 are connected to a processor 22 which receives signals from the buttons 20 when actuated.

The buttons 20 are disposed on the shelves 14 so that each storage location 18 is associated with a button 20. When an item is to be placed in or removed from a shelf 14, the button 20 in close proximity to the storage location 18 holding the item is actuated. Actuation of the button 20 sends a signal to the processor 22 to record removal of an item from or placement of an item into that particular storage location 18.

A return item button 23 is disposed at the end of each shelf 14. Actuation of the return item button 23 sends a signal to the processor 22 to place the buttons 20 on that particular shelf 14 in a credit mode. An item can then be returned to one of the storage locations 18 on that particular shelf 14, and the associated button 20 depressed to record replacement of the item.

A plurality of visual indicators 24 are also disposed on the shelves and near each of the buttons 20 so that each button 20 has a corresponding visual indicator 24. The visual indicators 24 are used to assist in locating an item to be removed from the dispensing unit 10. The processor 22 contains a list of all of the items held in the dispensing unit 10. From this list, a user can select the desired item to be removed by entering the selection into the processor 22. The processor 22 then sends a signal to actuate the visual indicator 24 in close proximity to the storage location 18 having the item.

The dispensing unit further includes a plurality of doors 26 which can be used to provide security for the items held in the unit 10. The doors 26 are preferably transparent and can be locked to prevent access to the items in the unit as described in more detail hereinafter.

The dispensing unit 10 has proven to be generally successful in maintaining an inventory of items dispensed from the unit. The invention as described in detail hereinafter provides improvements to dispensing units of the type described in FIG. 1. In one aspect of the invention, the storage locations are configured such that they can at least partially be pulled out or withdrawn from the dispensing unit. This configuration allows easier access to the storage locations. Exemplary apparatus for providing pull-out storage locations include drawers, racks, bins, hangars, and the like. Another particular advantage in using pull-out storage locations is that the storage locations can be further subdivided into a plurality of receptacles. The receptacles can be arranged in either one-dimensional or a multi-dimensional array. For example, in the case of drawers, dividers can be placed therein to form either a single row of receptacles or a plurality of rows. This allows the drawer to be subdivided in a desired manner according to the number and size of the receptacles required.

When providing the dispensing unit with a plurality of receptacles, a separate sensor can be provided for each receptacle to maintain an inventory of items either placed in or removed from that particular receptacle. For example, in the case of a drawer having a plurality of receptacles, each receptacle would be provided with a sensor so that when an item is withdrawn from one of the receptacles, the associated sensor can be actuated to record removal of the item from the receptacle. In a similar manner, the sensor could also be used to record placement of an item into the receptacle. Exemplary sensors for maintaining a record of the inventory of the items in the receptacles include touch-sensitive buttons, weight sensors, optical sensors, electromagnetic sensors, capacitative sensors, and the like.

In another aspect of the invention, a second set of sensors can be utilized to determine when the storage locations have been accessed. Use of storage location-associated sensors is particularly advantageous when having a plurality of storage locations with a plurality of receptacles in at least some of the storage locations. By providing the storage location-associated sensors, a common set of receptacle-associated sensors can be used for the receptacles of each of the storage locations rather than providing each receptacle with a separate sensor. When a particular storage location is accessed, the storage location-associated sensor sends a signal to the processor indicating that that particular storage location has been accessed. The processor can then use this information to set the common set of receptacle-associated sensors to correspond to the receptacle locations of the accessed drawer. After an item has been removed from a particular receptacle, the associated sensor can then be actuated to record removal of the item from that particular receptacle.

Providing a common set of receptacle-associated sensors is advantageous because it reduces the circuitry otherwise required to provide each receptacle with a separate sensor. Exemplary sensors for sensing when a particular storage location has been accessed include electromechanical switches, optical sensors, electromagnetic sensors, capacitative sensors, and the like.

In another particular aspect, the dispensing unit can be placed in a return item mode by actuating a return item sensor near each of the storage locations. Actuation of the return item sensor sends a signal to the processor to place the receptacle-associated sensors in return mode. An item can then be replaced and the associated receptacle sensor actuated to record replacement of the item.

Security for the items held in the dispensing unit can be provided by a variety of devices. One such device is a lock disposed near each pull-out storage location to prevent withdrawal of the drawer until certain information, such as user identification and patient identification information, has been entered into the processor. When the required information has been entered into the processor, the processor can send a signal to unlock all of the storage locations, or only the particular storage location having the item.

Locks can also be provided for the pull-out storage locations so that once a storage location has been withdrawn, all remaining storage locations are locked. Locking the remaining storage locations in this manner is advantageous in preventing confusion as to which receptacles correspond to the common set of receptacle-associated sensors. Since only one storage location can be accessed at a time, the receptacle-associated sensors will correspond to the receptacles of the withdrawn storage location.

In the case where all of the storage locations are unlocked by the processor, withdrawal of one of the storage locations will preferably cause all of the remaining storage locations to become locked. This ensures that only one storage location can be accessed at a time. When an item is removed from a receptacle having the item, the associated receptacle sensor can be actuated to record removal of the item. In a preferred aspect, if the user was diligent in recording removal by actuating the sensor, the processor sends the signal to unlock all of the storage locations so that a subsequent item can be removed. This allows a user access to all of the storage locations as long as the user is diligent in recording removal of an item from an accessed storage location. If a particular storage location has been withdrawn, and a receptacle-associated sensor was not actuated, all of the storage locations will become locked upon closure of the accessed storage location. To gain further access to the storage locations, the user will be required to re-enter identification information into the processor. An emergency by-pass switch can be provided on the unit so that all of the storage locations can be accessed without being required to enter identification information into the processor. Exemplary locking devices include electromechanical locks, electromagnetic locks, and the like.

When more than one item is to be removed from or placed into a particular receptacle, the associated receptacle sensor can be actuated according to the number of items to be removed or added. For example, if three items were to be removed from a particular receptacle, the sensor could be actuated three different times to record removal of the three items.

To assist the user in determining whether the sensor has been actuated, the sensor can optionally be provided with an audio indicator. For example, if the receptacle sensor were a touch-activated sensor, when the button is depressed, a beep would be produced to indicate that the button has been actuated. In addition, the number of items taken can be visually displayed on the screen of the associated processor. This serves as verification that the touch-activated sensor has been depressed the correct number of times.

Figure 2:
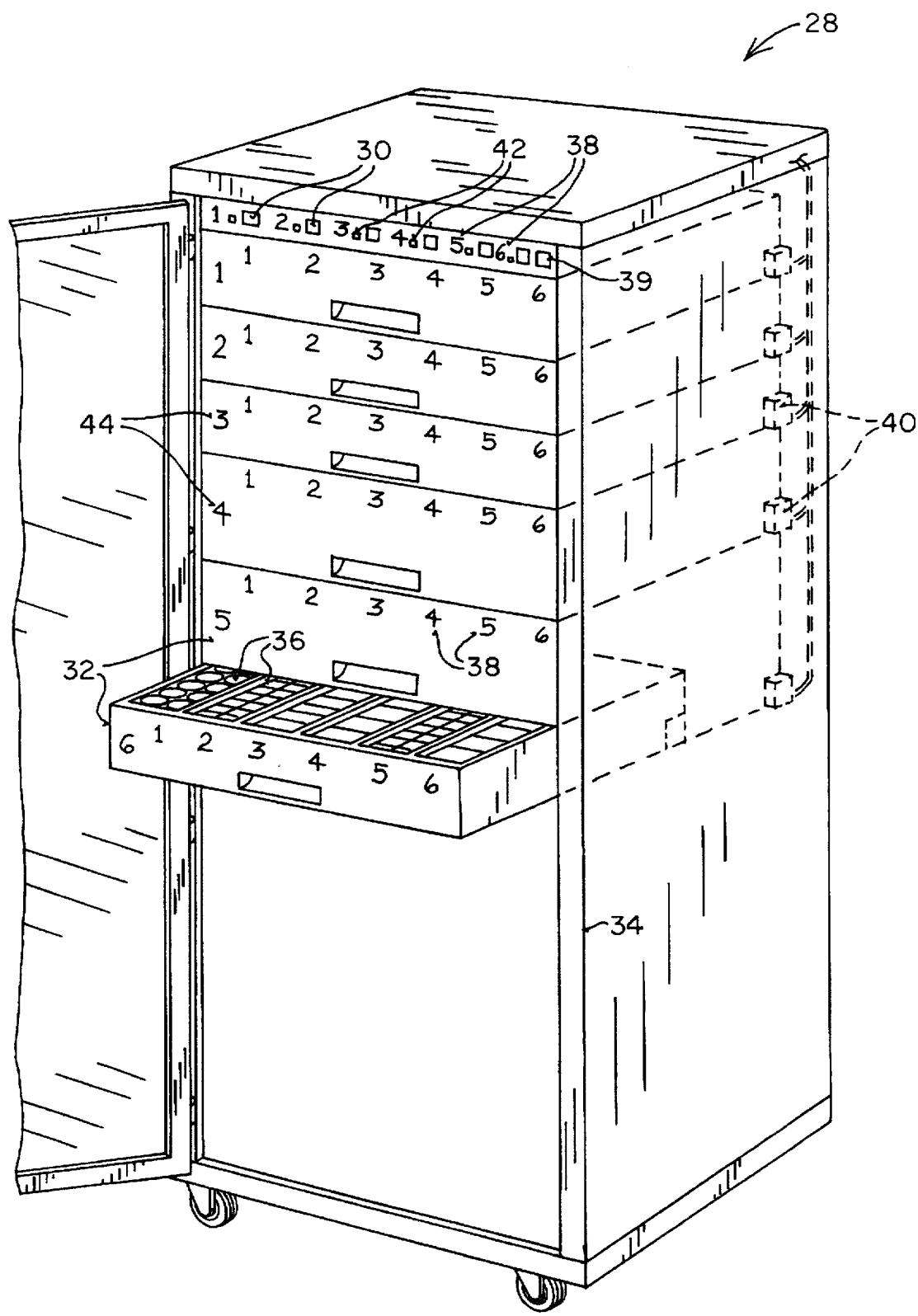
FIG. 2 illustrates a dispensing unit having a row of touch-sensitive buttons with corresponding visual indicators which correspond to a plurality of pull-out drawers below the row of buttons according to the present invention.

Referring now to FIG. 2, an exemplary embodiment of a dispensing unit 28 having a row of touch-sensitive buttons 30. The row of buttons 30 are common to a plurality of drawers 32 that are slidably disposed within a frame 34. The dispensing unit 28 can be a stand alone unit, or can alternatively be a portion of a larger dispensing unit of the type shown in FIG. 1. At least some of the drawers 32 are provided with a plurality of receptacles 36 for holding items.

Preferably, each button 30 will be provided with a unique button identification symbol 38, which will usually be a numeral. The receptacles 36 of each drawer 32 will preferably be provided with the same unique reference symbol 38 as its corresponding button 30. For example, as shown in FIG. 2, if the unit 20 is provided with six touch sensitive buttons 30, the buttons 30 can numbered one to six. Accordingly, the receptacles 36 for each of the drawers 32 will also be numbered from one to six (or any number less than six if there are fewer than six receptacles in the drawer). Of course, this assumes that the number of receptacles 36 will be equal to or less than the number of buttons 30 so that a receptacle 36 will always have a corresponding button 30.

Associated with each drawer 32 is a sensor 40 for sensing when the drawer 30 has been pulled out from the frame 34. Each of the sensors 40 and the buttons 30 are connected to a processor (not shown) for receiving signals from the sensors 40 or the buttons 30. When a particular drawer 32 is opened, the associated sensor 40 sends a signal to the processor indicating access to the drawer 32. The processor then sends a signal to set the buttons 30 to correspond to the receptacles 36 of the withdrawn drawer 32. An item can then be either placed into or removed from a particular receptacle and the button 30 having the same identification symbol 38 as the accessed receptacle 36 is touched to record removal or addition of the item to or from the dispensing unit 28. Additional items can also be removed or added from or to the receptacles 36 of the withdrawn drawer 32 with an inventory being maintained by selecting the associated button 30. Once the drawer 32 is closed, another can be withdrawn for removal of items in the same manner.

To assist in locating a particular item, a plurality of visual indicators 42 are disposed near each of the buttons 30 and each of the drawers 32 are provided with a unique drawer identification number 44 that correspond to the button identification symbols 38. With this configuration, the processor can send a signal to actuate the visual indicator 42 near the button 30 having the same identification symbol as the drawer identification symbol 44 for the drawer 32 having the item. Once the drawer 32 having the item is withdrawn, the processor can send another signal to actuate the visual indicator 42 near the button 30 having the same identification symbol as the receptacle 36 having the item. Alternatively, instead of providing the drawer identification symbols 44, a second set of visual indicators can optionally be provided on the drawers 32, with each drawer 32 having a separate visual indicator. The processor can then send a signal to actuate the drawer-associated visual indicator on the drawer 32 having the item.

The sensors 40 can optionally be combined with locking mechanisms, e.g., mechanical, electromagnetic, or the like, such that when one drawer 32 is pulled out the others are locked until the extended drawer 32 is returned. This insures that the buttons 30 will always correspond to the receptacles 36 of the withdrawn drawer 32.

A return item button 39 can be provided at the end of the row of touch-sensitive buttons 30 for placing the dispensing unit 28 in return mode. When return item button 39 is depressed, a signal is sent to the processor to place the touch-sensitive buttons in return mode. A drawer 32 can then be accessed, the item returned to the appropriate receptacle 36, and the associated touch-sensitive button 30 depressed to record replacement of the item.

Figure 3:
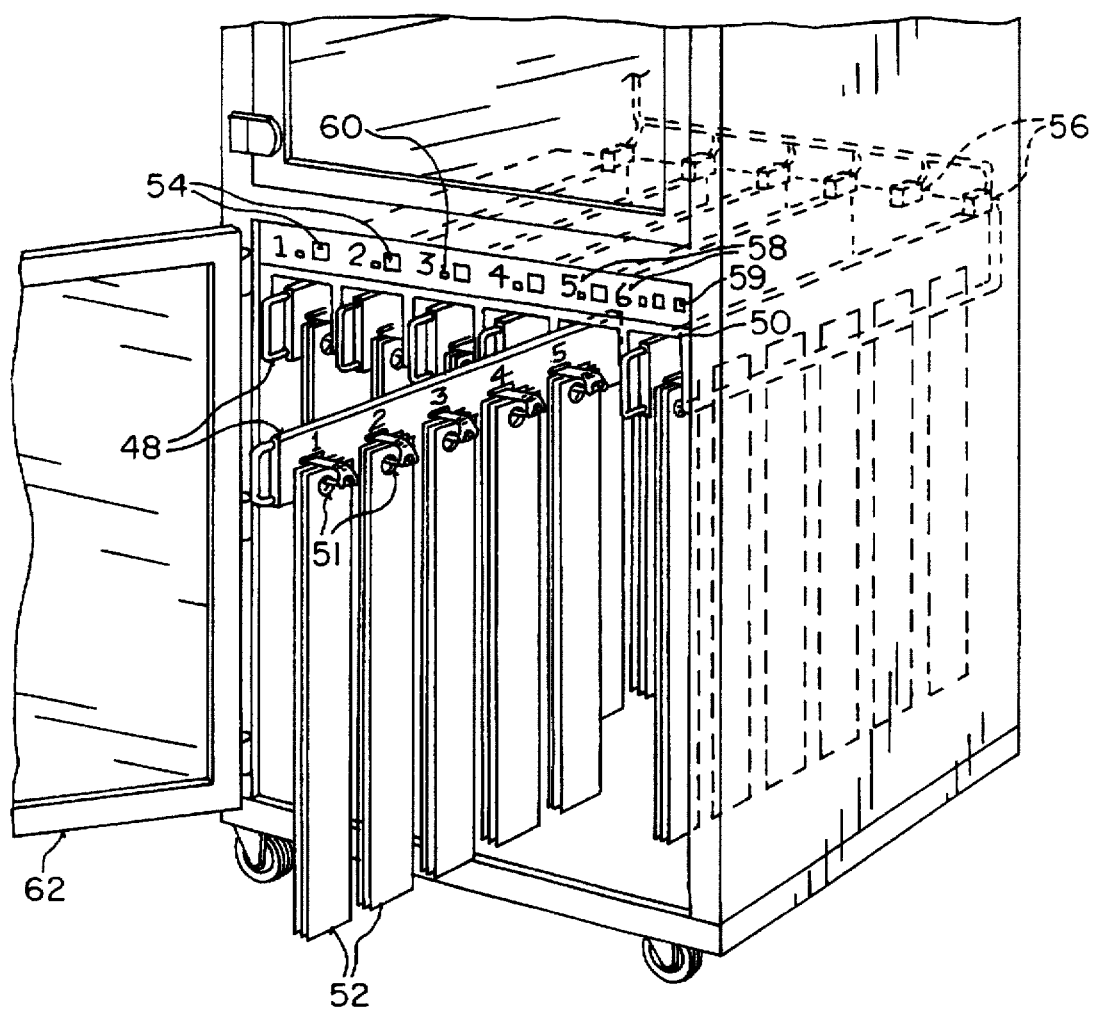
FIG. 3 illustrates a portion of a dispensing unit having a plurality of pull-out racks, with each rack being provided with a plurality of pegs for holding an inventory of items according to the present invention.

Shown in FIG. 3, is another embodiment of a dispensing unit 46 having a plurality of pull-out racks 48. The racks 48 are slidably disposed along a shelf 50. The dispensing unit 46 can be a stand alone unit, or can alternatively be used in a larger dispensing unit. At least some of the racks 48 include a plurality of pegs 51 for holding items 52. Exemplary items to be held on the pegs 51 include catheters which can be vertically hung from the pegs 51. Disposed near each of the racks 48 are a set of touch-sensitive buttons 54 for recording removal or addition of items. The dispensing unit 46 further includes a plurality of sensors 56 for sensing when the racks 48 have been withdrawn from the shelf 50. Both the buttons 54 and the sensors 56 are connected to a processor (not shown). Optionally, the sensors 56 can also be provided with locks so that when one rack 48 is pulled out the others are locked until the extended rack 48 is returned. This insures that the buttons 54 will always correspond to the pegs 51 of the withdrawn rack 48.

When a particular rack 48 is withdrawn from the shelf 50, a signal is sent from the sensor 56 to the processor to indicate withdrawal of the rack 48. The processor then sets the buttons 54 to correspond to the pegs 51 in a manner similar to the embodiment previously described in connection with FIG. 2. Also as previously described, a set of button identification symbols 58 can be provided for each button 54 and for each peg 51 so that removal of an item 52 from one of the pegs 51 can be recorded by touching the button 54 having the same identification symbol 58 as the peg 51 having the item 52.

A plurality of visual indicators 60 can be disposed near each of the buttons 54, with each button 54 having a separate visual indicator 60. The visual indicators 60 are used to identify which rack 48 and which peg 51 on the rack 48 contains the desired item. For instance, to locate a particular item, the processor can send a signal to the visual indicator 60 near the rack 48 having the item. Preferably, both the buttons 54 and the visual indicator 60 will be disposed above and generally aligned with each of the racks 48 so that each button 54 and each visual indicator 60 correspond to an aligned rack 48. Once the proper rack 48 has been identified and withdrawn, the processor can send a signal to the visual indicator 60 near the button 54 having the same identification symbol 58 as the peg 51 having the item. Alternatively, a second set of visual indicators could be disposed near each peg to indicate which peg 51 has the item.

A return item button 59 can be provided at the end of the row of touch-sensitive buttons 54 for placing the dispensing unit in return mode. When return item button 59 is depressed, a signal is sent to the processor to place the touch-sensitive buttons 54 in return mode. A rack 48 can then be accessed, the item returned to the appropriate peg 51, and the associated touch-sensitive button 54 depressed to record replacement of the item.

The dispensing unit 46 further includes a door 62 which can be used to provide security for the items held in the unit 46 as described in more detail hereinafter.

Figure 3A:
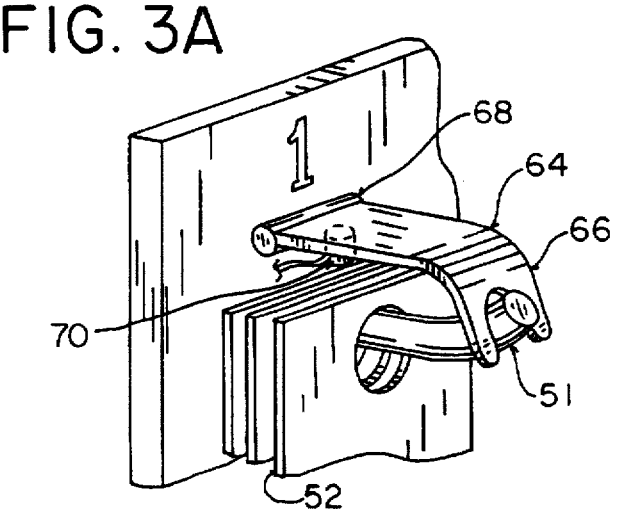
FIG. 3A is a detailed view of one of the pegs of FIG. 3 and further showing a sensor associated with the peg for sensing removal of an item from the peg according to the present invention.

Referring to FIG. 3A, a detailed view of one of the pegs 51 of the dispensing unit 46 is shown. The peg 51 is provided with a sensor 64 for sensing when one of the items 52 has been removed from or added to the peg 51. The sensor includes a lever 66 that is connected to the rack 48 by a hinge 68. A microswitch 70 is disposed beneath the lever 66 to detect when the lever 66 has been lifted from the peg 51. When the microswitch 70 is actuated, a signal is sent to the processor indicating that one of the items 52 has been either removed from or placed onto the peg 51. This embodiment is particularly advantageous because it eliminates the need for the touch-sensitive buttons 54 described in FIG. 3. The sensor 64 is able to maintain an inventory of the items 52 without requiring the user to touch one of the buttons 54.

Figure 3B:
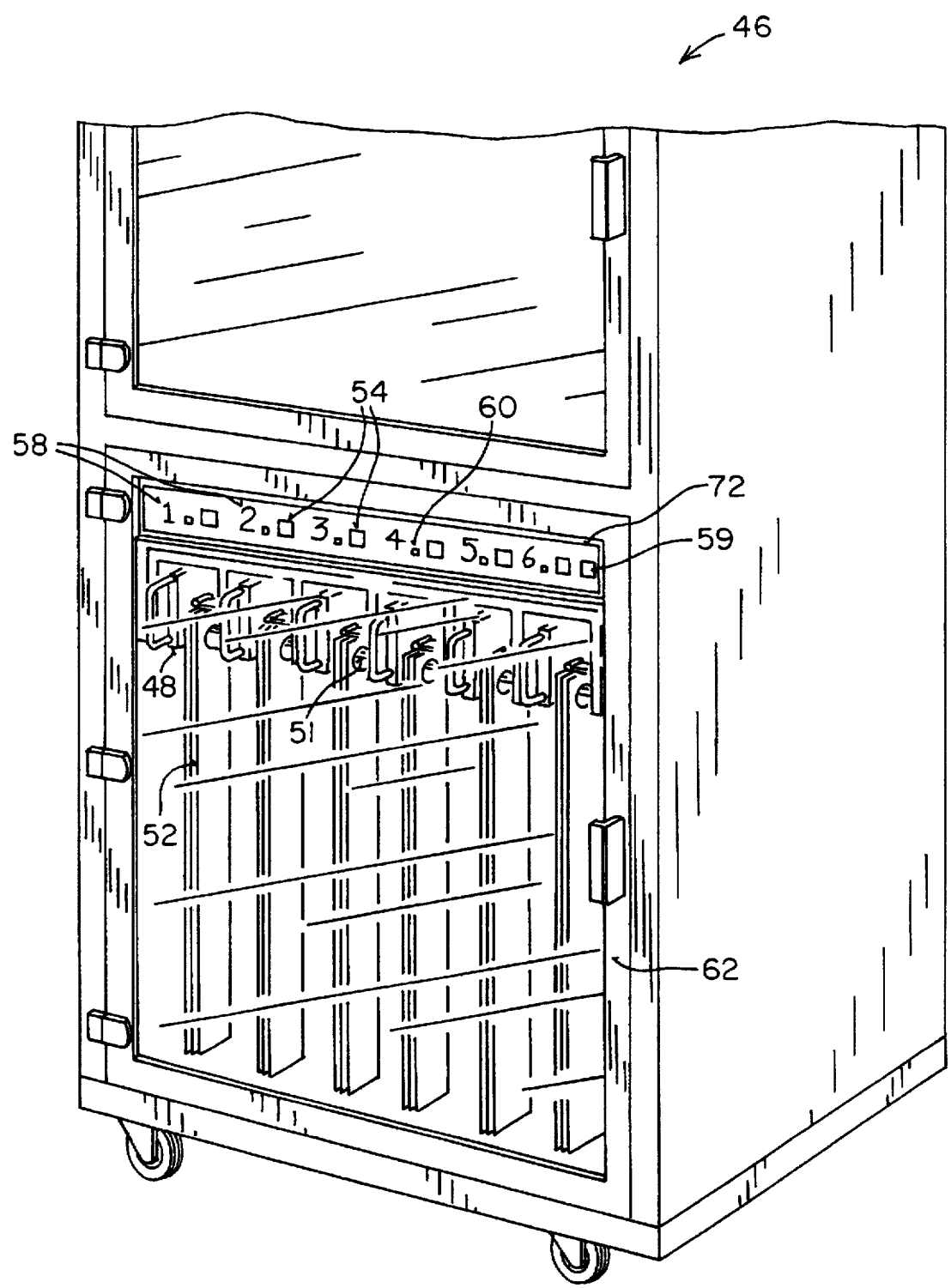
FIG. 3B is an alternative embodiment of the dispensing unit of FIG. 3 showing a door that is provided with an aperture to allow access to the touch-sensitive buttons and visual indicators when the door is closed.

Shown in FIG. 3B is an alternative embodiment of the dispensing unit 46 having an aperture 72 in the door 62. The aperture 72 is disposed near the touch-sensitive buttons 54 so that the buttons 54 are accessible even when the door 62 is closed. As described generally in co-pending U.S. application Ser. No. 08/250,223, filed May 27, 1994 (Attorney Docket No. 16166-1-1), the disclosure of which is herein incorporated by reference, the door 62 is locked until appropriate identification information, such as item identification information, has been entered into the processor. When the required information has been entered into the processor, a signal is sent to unlock the door 62 to provide access to the items in the unit 46. One way to enter item identification information into the processor is to actuate the buttons 54. The aperture 72 provides access to the buttons 54 when the door 62 is closed and locked so that one of the buttons 54 can be selected to indicate that an item is to be removed. Once the button 54 is selected, the door 62 is unlocked to allow access to the items.

In an exemplary method, access to one of the items 52 held in the unit 46 is as follows. After entering user identification information and patient identification information into the processor, the user selects the rack 48 having the item 52 by pressing the button 54 disposed above the rack 48. In one particular aspect, the visual indicator 60 will then be actuated to remind the user which rack 48 was selected. Actuation of the button 54 unlocks the door 62. When the door 62 is opened, the user can pull out the selected rack 48 and remove the item 52 from the peg 51. Removal of the item 52 is then recorded by pressing the button 54 having the same identification number 58 as the peg 51 having the item 52.

Figure 3C:
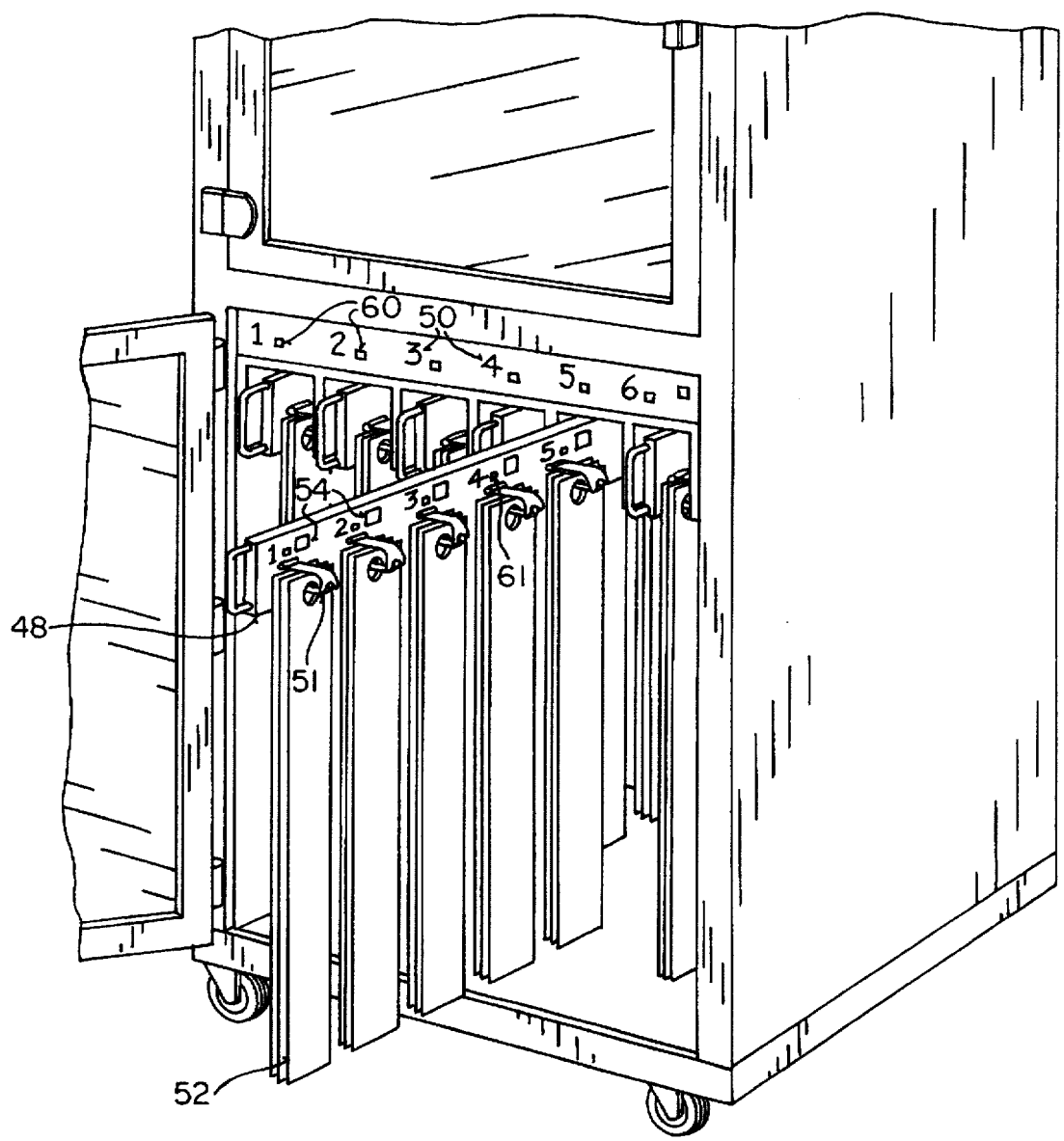
FIG. 3C is a further alternative embodiment of FIG. 3 showing the touch-sensitive buttons and visual indicators disposed along the racks according to the present invention.

Referring to FIG. 3C, another alternative embodiment of the dispensing unit 46 of FIG. 3 is shown with the touch-sensitive buttons 54 being disposed along the racks 48. Each peg 51 is provided with its own button 54 so that removal or addition of an item 52 to or from the peg 51 can be recorded by simply touching the button 54 disposed in closest proximity to the peg 51 having the item 52. To assist in locating the correct rack, visual indicators 60 can be disposed above each of the racks 48. Actuation of one of the visual indicators 60 signifies which rack 48 has the item to be removed. Once the rack 48 has been withdrawn, the peg 51 having the item 52 can be visually located by actuating the visual indicator 60 having the same button identification symbol as the peg 51 having the item 52. Alternatively, a second set of visual indicators 61 can be provided near each of the buttons 54 to indicate which peg 51 has the item.

Figure 4:
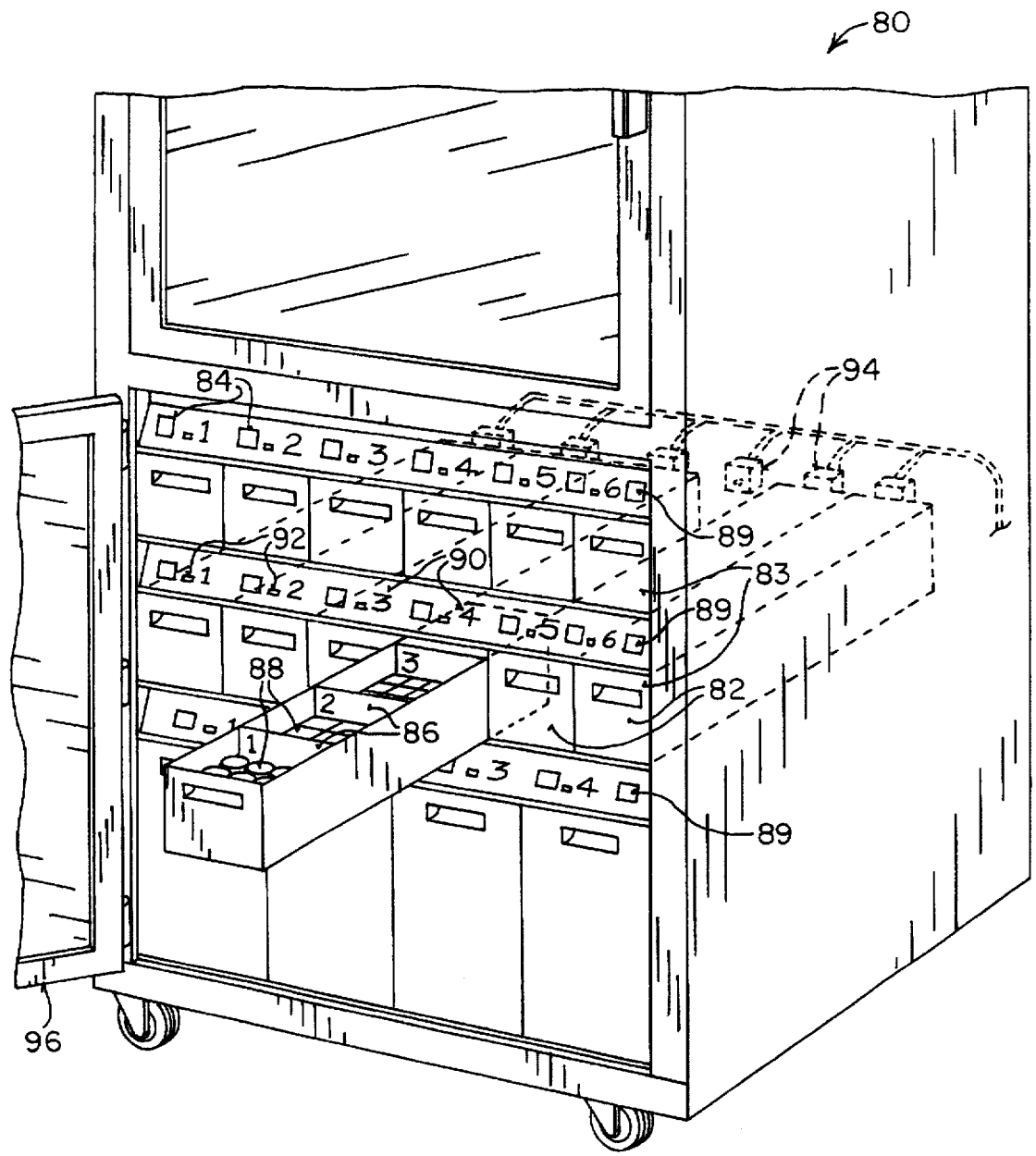
FIG. 4 illustrates a portion of a dispensing unit having a row of touch-sensitive buttons and visual indicators, and a plurality of drawers disposed below the buttons with at least some of the drawers having a plurality of receptacles according to the present invention.

Shown in FIG. 4 is another embodiment of a dispensing unit 80 having a plurality of drawers 82 disposed along rows 83. The dispensing unit 80 can be a stand alone unit, or can alternatively be part of a larger dispensing unit. Each row 83 of drawers 82 has an associated row of touch-sensitive buttons 84 disposed on a panel 86, with each button 84 being generally aligned with a drawer 82. At least some of the drawers 82 include dividers 86 for dividing the drawers 82 into a plurality of receptacles 88. Optionally, a plurality of button identification symbols 90 can be provided for each of the buttons 84 and for each of the receptacles 88 as previously described in FIGS. 2 and 3. The unit 80 further includes a plurality of visual indicators 92, with each button 84 having an associated indicator 92.

The dispensing unit 80 operates in a manner similar to the dispensing unit 46 of FIG. 3 with the drawers 88 corresponding to the racks 48 and the receptacles 88 corresponding to the pegs 51. A plurality of sensors 94 are disposed near each drawer 82 and connected with a processor (not shown) so that withdrawal of one of drawers 82 sends a signal to the processor to indicate access of that particular drawer. The processor then sets the row of buttons 84 over the withdrawn drawer 82 to correspond to the particular receptacles 88 of the withdrawn drawer 82. Removal of an item or placement of an item into one of the receptacles 88 can be recorded by actuating the button 84 having the same identification symbol as the accessed receptacle 88. A return item button 89 is provided at the end of the row of touch-sensitive buttons 84 for placing the dispensing unit 80 in return mode as previously described.

The dispensing unit 80 can further be provided with a door 96 for providing security to the items held in the unit 80. The door 96 can be provided with a plurality of apertures to correspond to the buttons 84 in a manner similar to the apertures previously described in connection with FIG. 3B.

Figure 5:
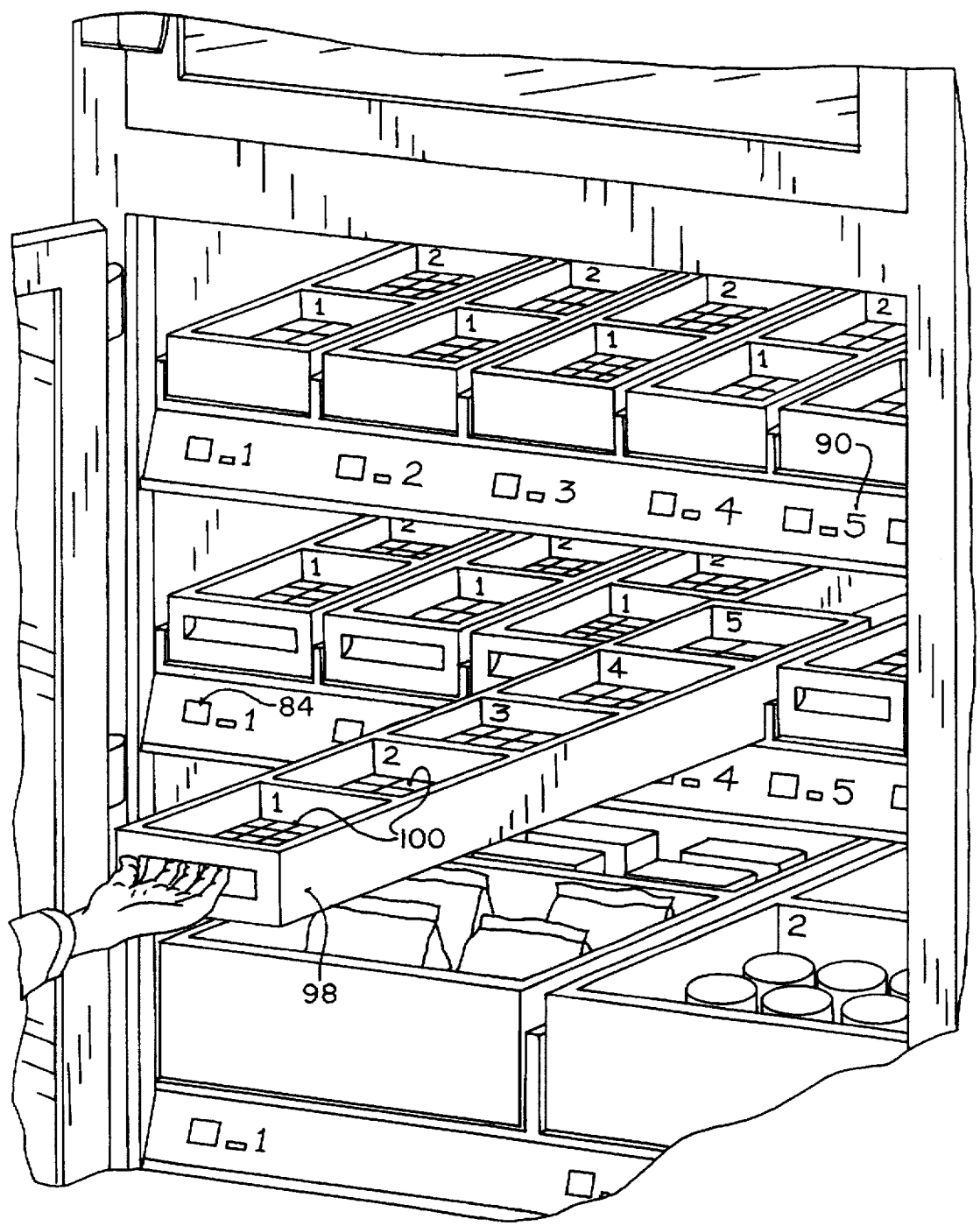
FIG. 5 illustrates a portion of a dispensing unit having a row of touch-sensitive buttons and visual indicators, and a plurality of bins disposed above the buttons on a shelf, with at least some of the bins having a plurality of receptacles.

Referring to FIG. 5, the dispensing unit 80 can be provided with a plurality of removable bins 98 instead of or in addition to the drawers 82 described in FIG. 4. Removal of one of the bins 98 is detected by a sensor (not shown) near the bin 98 which sends a signal to the processor to set the buttons 84 to correspond to a set of receptacles 100 in the bin 98. To record removal of an item from the withdrawn receptacle 100, the button 84 having the same identification symbol 90 as the receptacle 100 having the item is actuated.

Figure 6:
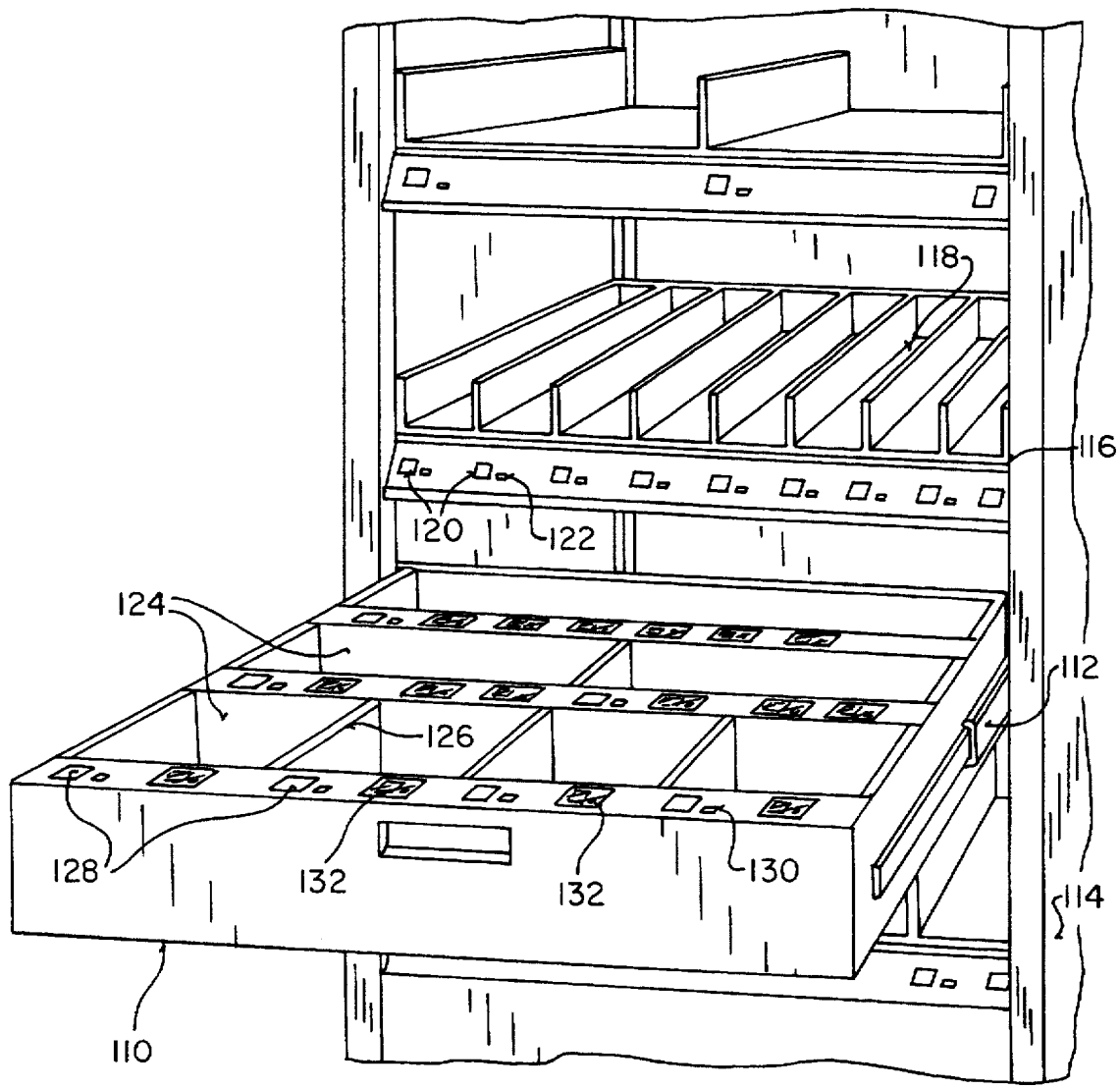
FIG. 6 illustrates a portion of a dispensing unit having a pull-out drawer with a plurality of receptacles therein, with each receptacle being provided with a touch-sensitive button and visual indicators.

Turning to FIG. 6, an exemplary drawer 110 for a dispensing unit of the type previously described in connection with FIG. 1 will be described. The drawer 110 is slidably mounted by a sliding mount 112 to a frame 114. The frame 114 is the same frame used to hold the shelf 116. The shelf 116 is essentially identical to the shelves 14 previously described in connection with FIG. 1 and includes a plurality of storage locations 118, a plurality of touch-sensitive buttons 120, and a plurality of visual indicators 122.

The drawer 110 can be subdivided into a plurality of receptacles 124 by dividers 126. The dividers 126 are adjustable so that the number and size of the receptacles 124 can be varied depending on the size or number of items to be held in the receptacles 124. Disposed near each receptacle 124 is a touch-sensitive button 128 and a corresponding visual indicator 130. Button covers 132 can be provided for covering unnecessary buttons so that only one button 120 will be associated with each receptacle 124.

The buttons 120 and the visual indicators 130 are connected to a processor (not shown). When an item is removed from or placed into a particular receptacle 124, removal or placement of the item can be recorded by touching the button 128 disposed adjacent the receptacle 124 having the item. To assist in locating the receptacle 124 having the item, the processor can send a signal to actuate the visual indicator 130 disposed near the receptacle 124 having the item.

Figure 7:
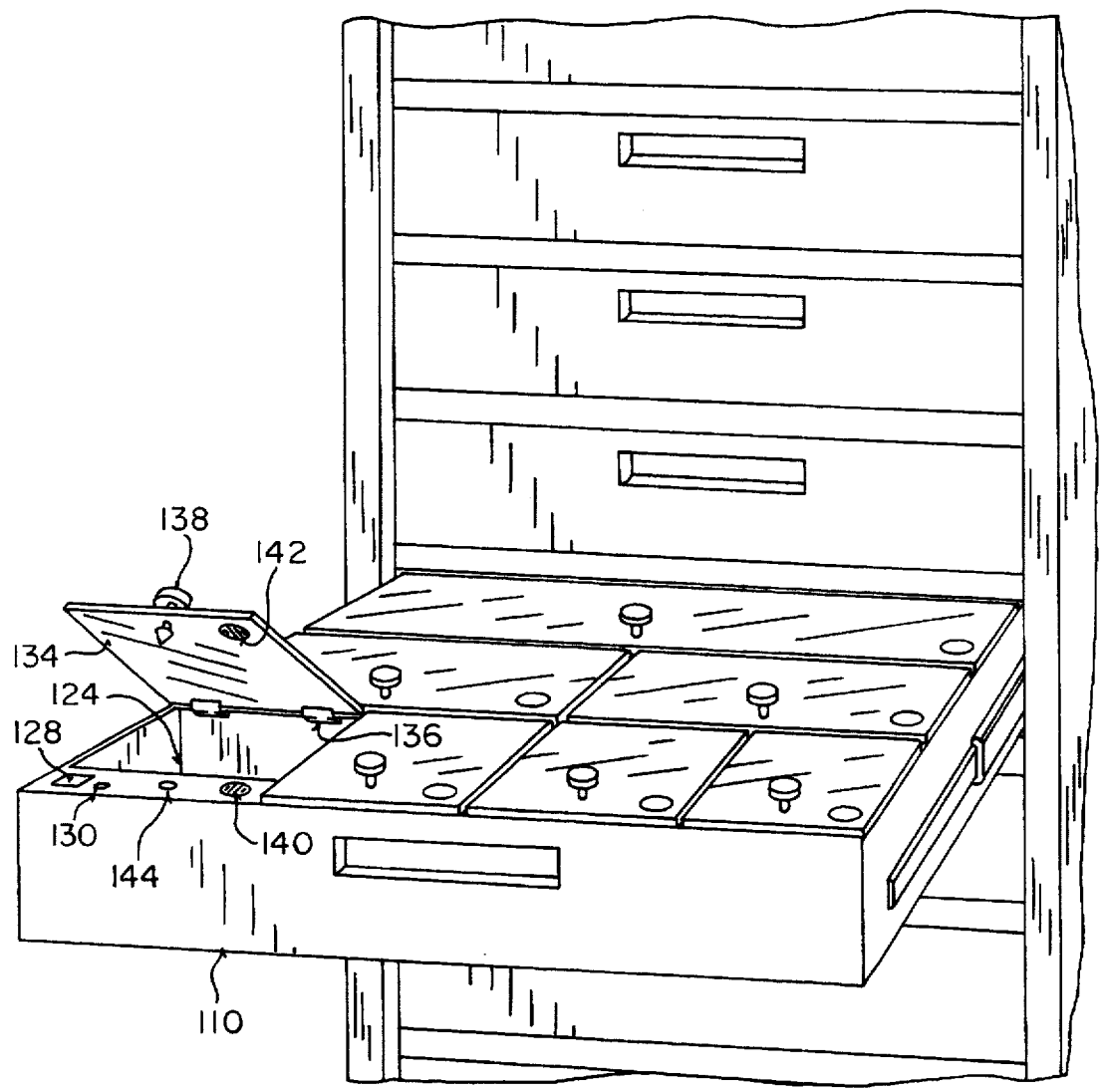
FIG. 7 illustrates an alternative embodiment of FIG. 6 showing a plurality of covers for each of the receptacles.

As shown in FIG. 7, the drawer 110 can be provided with a plurality of receptacle covers 134. The covers 134 are preferably connected to the drawer 110 by a hinge 136 so that the covers 134 can be lifted from the drawer 110 to obtain access to the receptacles 124. The covers 132 can be provided with a knob 138 to assist in lifting the cover 134.

A sensing mechanism comprising an electromagnetic sensor 140 and a magnet 142 are provided to sense when the cover 134 has been lifted. Alternatively, an optical sensor, a capacitative sensor, or the like could also be used to sense when the cover 142 has been lifted.

The electromagnetic sensor 140 sends a signal to the processor to indicate that the cover 134 has been lifted. This information can be used to record removal of an item from the receptacle 124 or can be stored and compared with item removal information entered by the button 128. If the cover 134 has been lifted more times than the button 128 was actuated, a report can be generated indicating that further user training or supervision may be required.

Preferably, the covers 134 will be substantially transparent so that the items in the receptacles 124 and the visual indicators 130 can be viewed with the cover 134 closed.

The drawer 110 can be provided with a lock 144 for locking the cover 134 until user identification and patient identification information have been entered into the processor. When the required information has been entered, the processor will send a signal to unlock the cover 134 making the receptacle 124 available for access.

Figure 8:
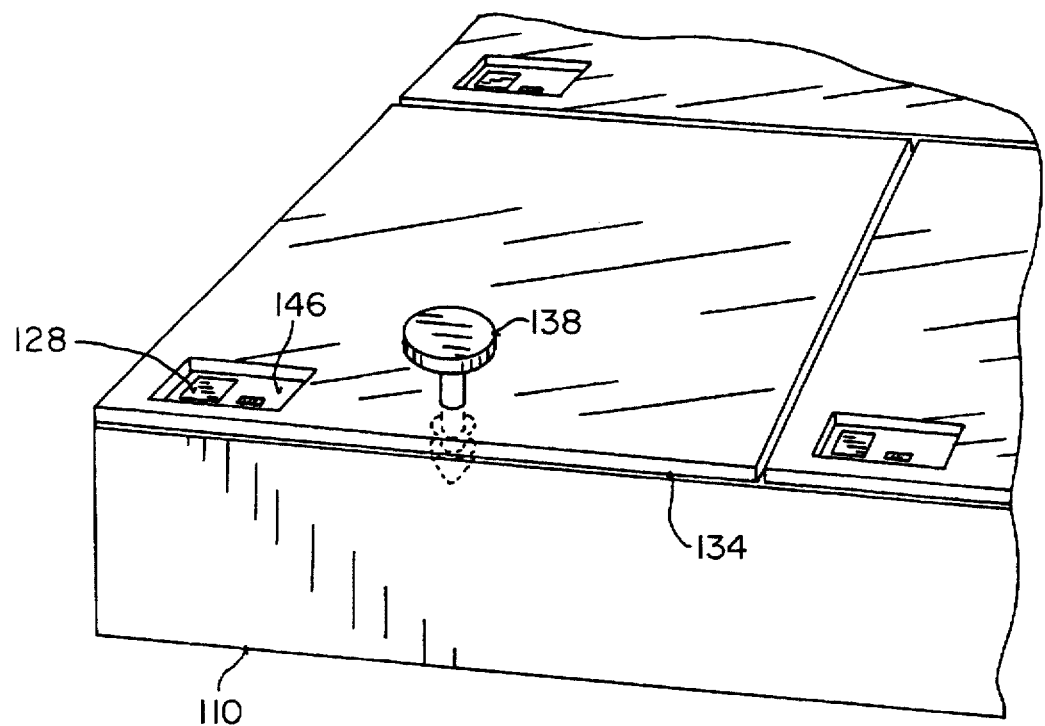
FIG. 8 is an alternative embodiment of the drawer of FIG. 7 showing an aperture in the cover to allow access to the touch-sensitive button and observation of the associated visual indicator when the cover is closed.

An alternative embodiment of the drawer 110 is shown in FIG. 8. One of the covers 134 is provided with an aperture 146 so that the button 128 is accessible when the cover 134 is closed. The aperture 146 is large enough to allow access to the button 128 but small enough to prevent access to the receptacle 124. When providing the cover 134 with the aperture 146, the cover 134 will preferably remain locked until the button 128 is actuated to indicate an item is to be removed. This ensures that the removal of at least one item will be recorded before the item is made available for removal. Locking the cover 134 also serves as a reminder that the buttons 128 should be depressed each time an item is withdrawn from a receptacle 124 and also ensures a record of removed items so that stock can be replenished.

The processor can also be configured to lock the covers 134 and deny access to selected receptacles 124 based on the user identification information entered into the processor. Depending upon the user's identification, access will only be provided to the receptacles 124 to which that particular user is entitled.

Figure 9:
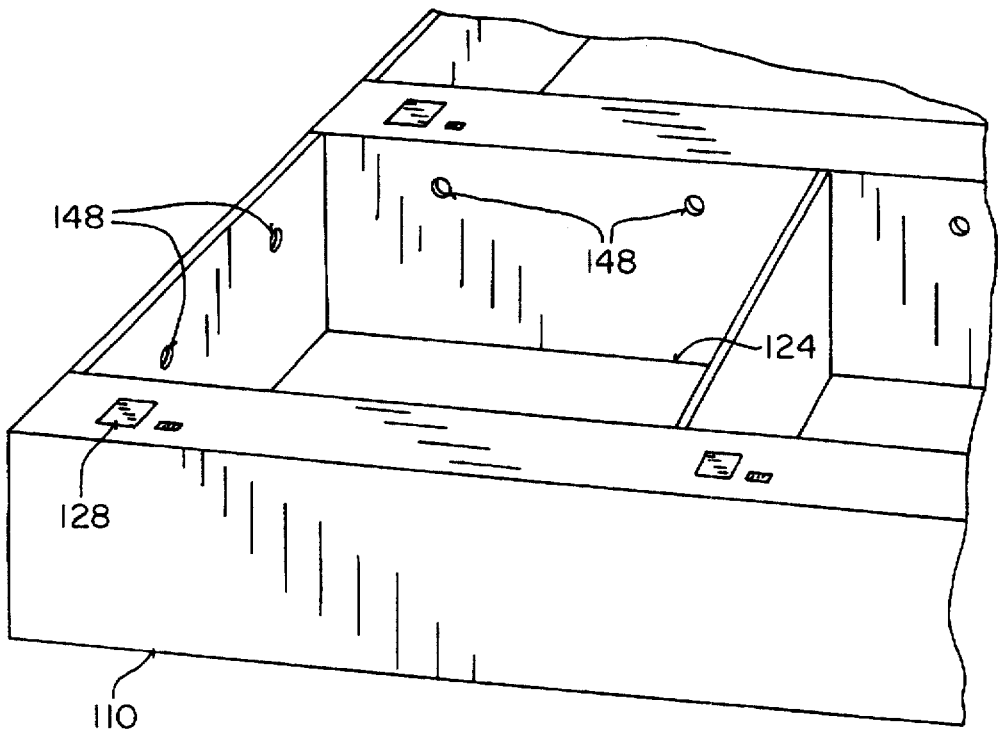
FIG. 9 illustrates another alternative embodiment of the drawer of FIG. 6 showing a plurality of optical sensors disposed within the drawer for sensing access to the receptacles.

Referring to FIG. 9, the drawer 110 is provided with a plurality of receptacle sensors 148 arrayed along the sides of the receptacle 124. The sensors 148 sense when a hand has entered the receptacle 124 to take or add an item. Each time the sensor is actuated, an entry is recorded. The touch sensitive button 128 can optionally be provided and used to register the number of items taken. If no items have been taken, i.e. if no buttons 128 have been actuated, the sensors 148 can be used to record that the receptacle 124 has been accessed by the user. If the receptacle 124 has been accessed and the button 128 has not been actuated, then the processor can record removal of items based on the number of entries into the receptacles 124.

Figure 10:
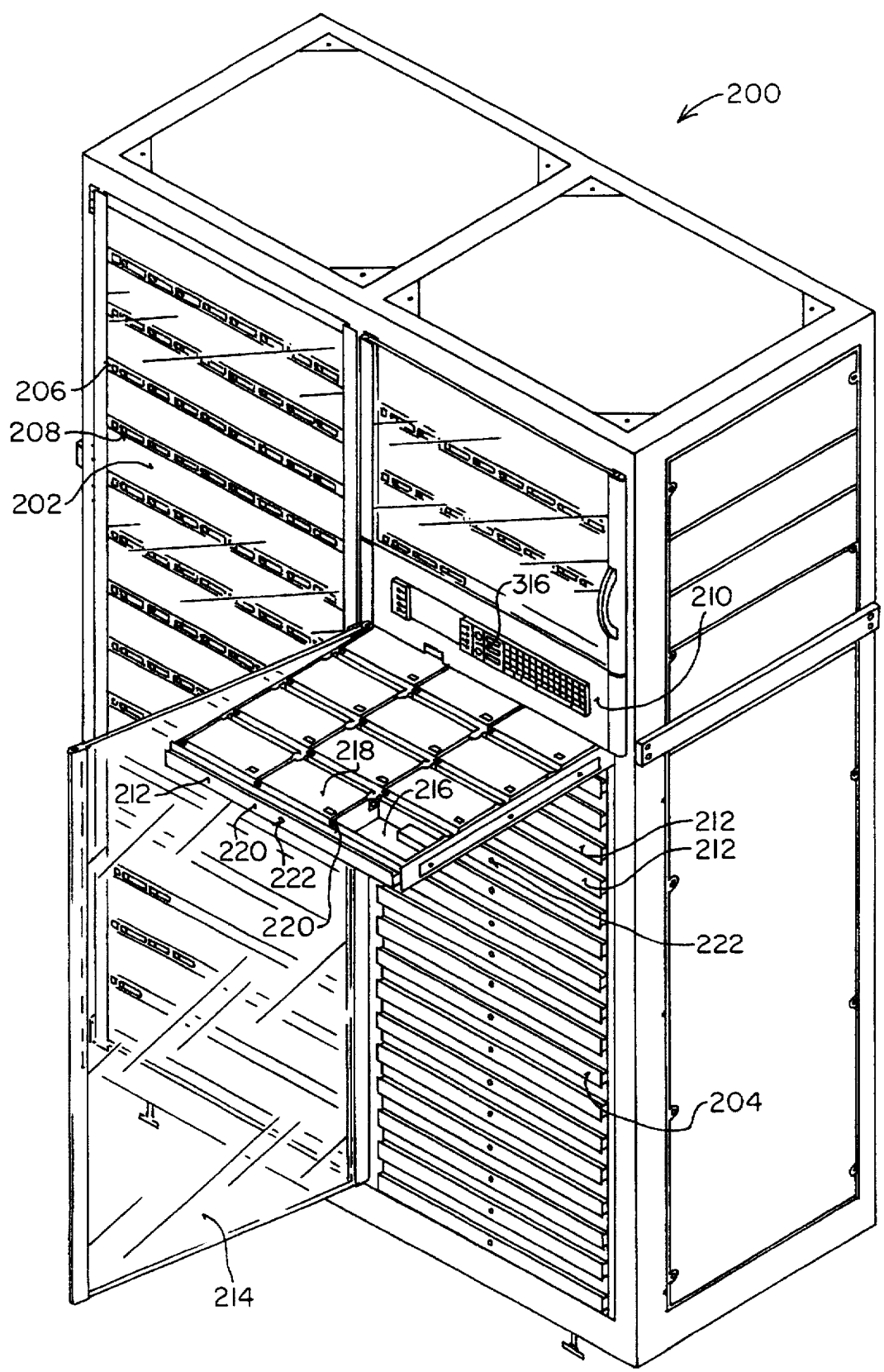
FIG. 10 illustrates an exemplary embodiment of a dispensing unit particularly useful in dispensing pharmaceutical items according to the present invention.

A further alternative embodiment of an exemplary dispensing unit 200 is shown in FIG. 10. The dispensing unit 200 is divided into a supply zone 202 and a pharmaceutical zone 204. The supply zone 202 includes a plurality of shelves 206 that are subdivided into a plurality of storage locations as previously described in connection with the dispensing unit 10 of FIG. 1. A plurality of touch-sensitive item buttons 208 are provided on each shelf 206 for recording the transfer of an item to or from the storage location on the shelf 206 in the manner previously described in connection with the dispensing unit 10 of FIG. 1. The dispensing unit 200 further includes a processor 210 that is in communication with the buttons 208 for recording transfer information in the manner previously described with the processor 22 of the dispensing unit 10 of FIG. 1. As will be described in greater detail hereinafter, the processor 210 is further employed to record transfer and other information for the pharmaceutical zone 204.

The pharmaceutical zone 204 includes a plurality of pull-out drawers 212. A door 214 may optionally be provided over the drawers 212. The number of drawers 212 (as well as the size of the pharmaceutical zone 204) are variable depending upon the number of pharmaceutical items to be held in the dispensing unit 200. Optionally, the dispensing unit 200 can be provided with only a pharmaceutical zone 204 so that only pharmaceutical items are held in the dispensing unit 200. Both the door 214 and the drawers 212 may be provided with locks so that access can selectively be denied to the entire pharmaceutical zone 204 or to selected drawers 212. Limiting access is preferably best accomplished by including a database in the processor 210 having a list of names of medical personnel along with the names of items to which each person may be afforded access. Upon entering of a nurse's identification information into the processor 210, the nurse's identification information is compared with the information in the database to determine which areas of the dispensing unit 200 that the nurse may access. The processor 210 can then send a signal to unlock the door 214 or selected drawers 212 for which the nurse may be afforded access.

At least some of the drawers 212 are provided with a plurality of bins 216 that are each preferably covered with a lid 218. A touch-sensitive bin button 220 is located adjacent each of the bins 216 and optionally may be configured to operate essentially identical to the buttons 220 on the dispensing unit 10 of FIG. 1 to record the transfer of items to or from the bins 216. Each of the buttons 220 can optionally be provided with a light source so that the button 220 can additionally serve as a visual indicator to locate the bin 216 having an item that is selected from the processor 210. Also included on each drawer 212 is a touch-sensitive drawer button 222. The drawer button 222 operates in a similar manner as the bin button 220 except that the drawer button 222 is employed to request the unlocking of the associated drawer 212. When the drawer button 222 is touched, a signal is sent to the processor 210 so that the processor 210 can send a return signal to unlock the drawer 212 and also to produce a record of access to that particular drawer 212. Optionally, the drawer button 222 can also function as a visual indicator to assist in locating the drawer 212 having an item requested from the processor 210. Optionally, each lid 216 (or selected lids) may be provided with a lock to secure the lid 218 in a closed position until receiving an unlock signal from the processor 210 as described hereinafter.

The pharmaceutical zone 204 may be configured to provide various levels of security to the items held in the bins 216. Security is provided by requiring certain information to be entered into the processor 210 before locks on the door 214, the drawers 212, or the lids 218 will be unlocked. For example, to gain initial access to the drawers 212, the nurse will preferably be required to enter in both nurse and patient identification information. After entering such information, a signal is sent from the processor 210 to unlock the door 214 (if provided). The ability to access a desired drawer 212 will then vary depending upon the particular security level of the drawer 212. In one aspect, at least some of the drawers 212 will be configured to be "low security" drawers which may be accessed by simply touching the drawer button 222 to unlock the requested drawer 212. The low security drawer 212 will have all of its bins 216 freely accessible once the drawer 212 is open. Since access to the bins 216 is freely afforded, the lids 218 may optionally be removed. After removal of an item, the associated bin button 220 is touched to record the transaction as previously described. After removal of the item or items, the nurse closes the drawer 212 before requesting that another drawer be opened. In the event that the first drawer is not closed, a sensor (not shown) will detect that the first drawer has not been closed and the user will be instructed to close the first drawer before trying to select another drawer.

At least some of the drawers 212 can be configured to be "medium security" drawers which may be accessed in essentially the same manner as the low security drawers except that the lids 218 will have an associated sensor (not shown) to detect when the lid is open. The lids 218 are preferably transparent so that the nurse may easily be able to identify the items in the bins 216. Upon removal of a lid 218, a signal is sent to the processor 210 to produce a record of access to the drawer 218. This record may then be compared to the record produced when the associated touch-sensitive bin button 220 is depressed to record removal of an item. A report may then be generated indicating any discrepancies between access to the bins 216 and the recordation of a transfer using the buttons 220.

In a further aspect, at least some of the drawers 212 can be configured to be "high security" drawers where the lids 218 are opaque and access cannot be obtained until the nurse enters item identification information into the processor 210 for the particular item to be dispensed. Hence, if the nurse fails to input the item identification information into the processor 210, the drawer 212 will remain locked even if the drawer button 222 is selected. If such item identification information has been input, the drawer 212 will unlock when the drawer button 222 is selected. The high security drawers further differ from the medium security drawers in that all of the lids 218 are locked except for the lid 218 covering the bin 216 having the requested item. When the drawer 212 is opened, only the bin 216 having the requested item will have its lid 218 unlocked so that the nurse can only gain access to the requested item.

Figure 10A:
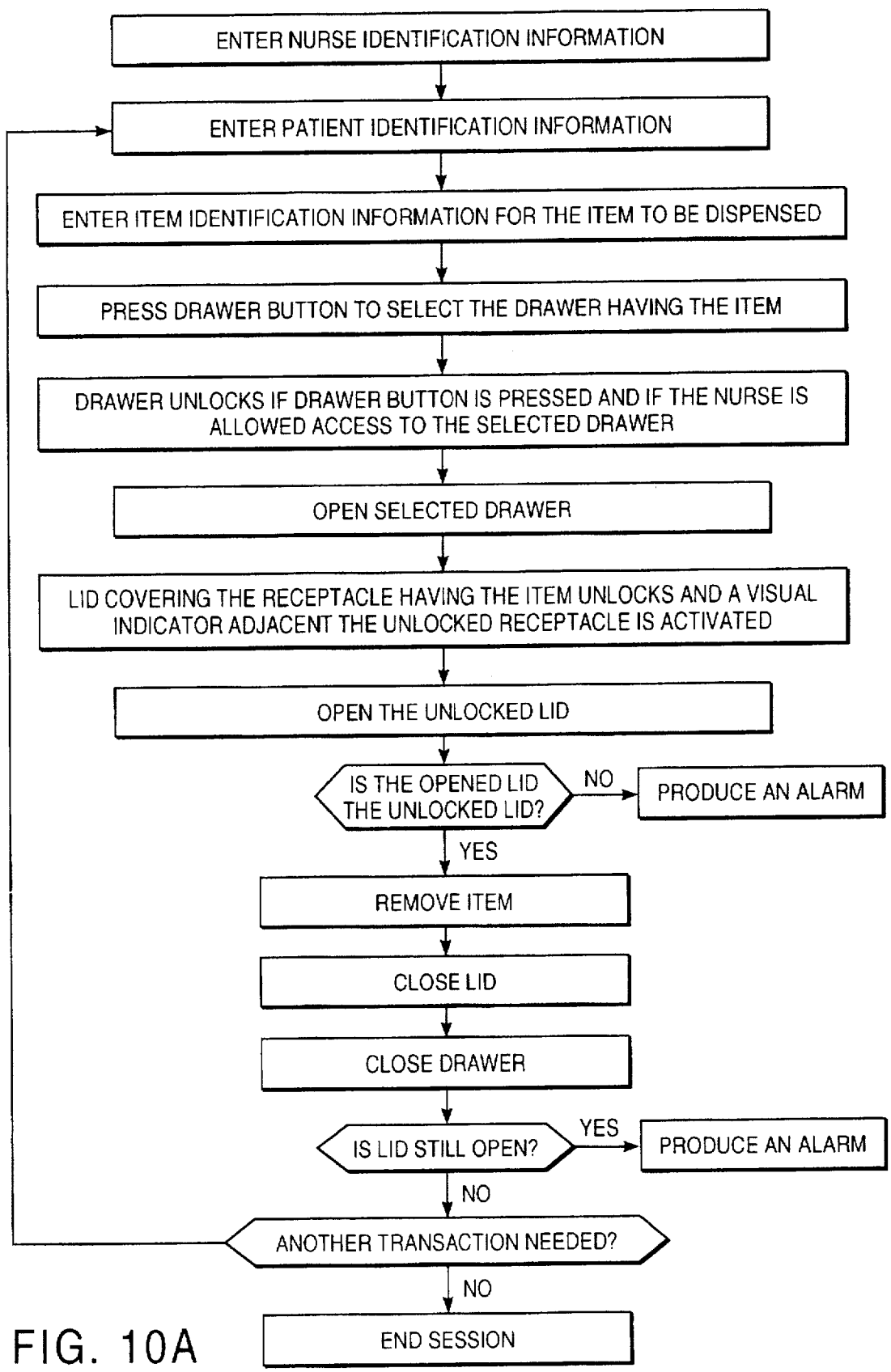
FIG. 10A is a flowchart of an exemplary method for dispensing pharmaceutical items from the dispensing unit of FIG. 10 according to the present invention.

Referring to FIG. 10A, an exemplary method for removing an item from a high security type drawer will be described. Initially, both nurse and patient identification information are entered into the processor 210. Patient identification information will usually be entered by selecting the patient from a list of patients already in the hospital. Such information will preferably be electronically transferred from the hospital's admission computer system. Item identification information for the item to be dispensed is then input into the processor 210. The drawer button 222 having the requested item is then pressed to request that the drawer 212 be unlocked. Optionally, the drawer button 222 can be lighted to assist the user in locating the drawer 212 having the item. After the selected drawer 212 is unlocked, the drawer 212 is retracted and the lid covering the bin 216 having the requested item is unlocked. Optionally, the bin button 220 adjacent the unlocked bin 216 will be lighted to assist in locating the bin 216 having the requested item. The unlocked lid 218 is then opened and the requested item removed. Since item identification information has already been entered into the processor 210, the bin button 220 need not be depressed to record the transaction.

In the event that the nurse attempts to open a lid 218 that is not unlocked, an alarm will be produced. After the item has been removed, the lid 218 and the drawer 212 are closed. If the lid is left open upon closure of the drawer 212, an alarm will be produced to remind the nurse to close the lid 218. After the drawer 212 is closed, the nurse can proceed with another transaction by entering the appropriate information into the processor 210 and repeating the previously described steps.

The pharmacy zone 204 may alternately be configured to provide various levels of security for the items held therein based on information that is directly input into the processor 210 prior to access of removal of any items. Such information will usually take the form of nurse identification information, item identification, and in some cases item quantity information. Optionally, patient identification information may also be input. In this way, a nurse may "preselect" both the type and quantity of items that are to be removed before accessing a drawer or bin or other storage location. If the processor 210 determines that the nurse may have access to such items, the nurse will be guided via visual indicators to the appropriate storage locations. Then, the method of removal will vary depending on the particular security level required for each item. Such methods are illustrated in FIGS. 10B–10D.

Figure 10B:
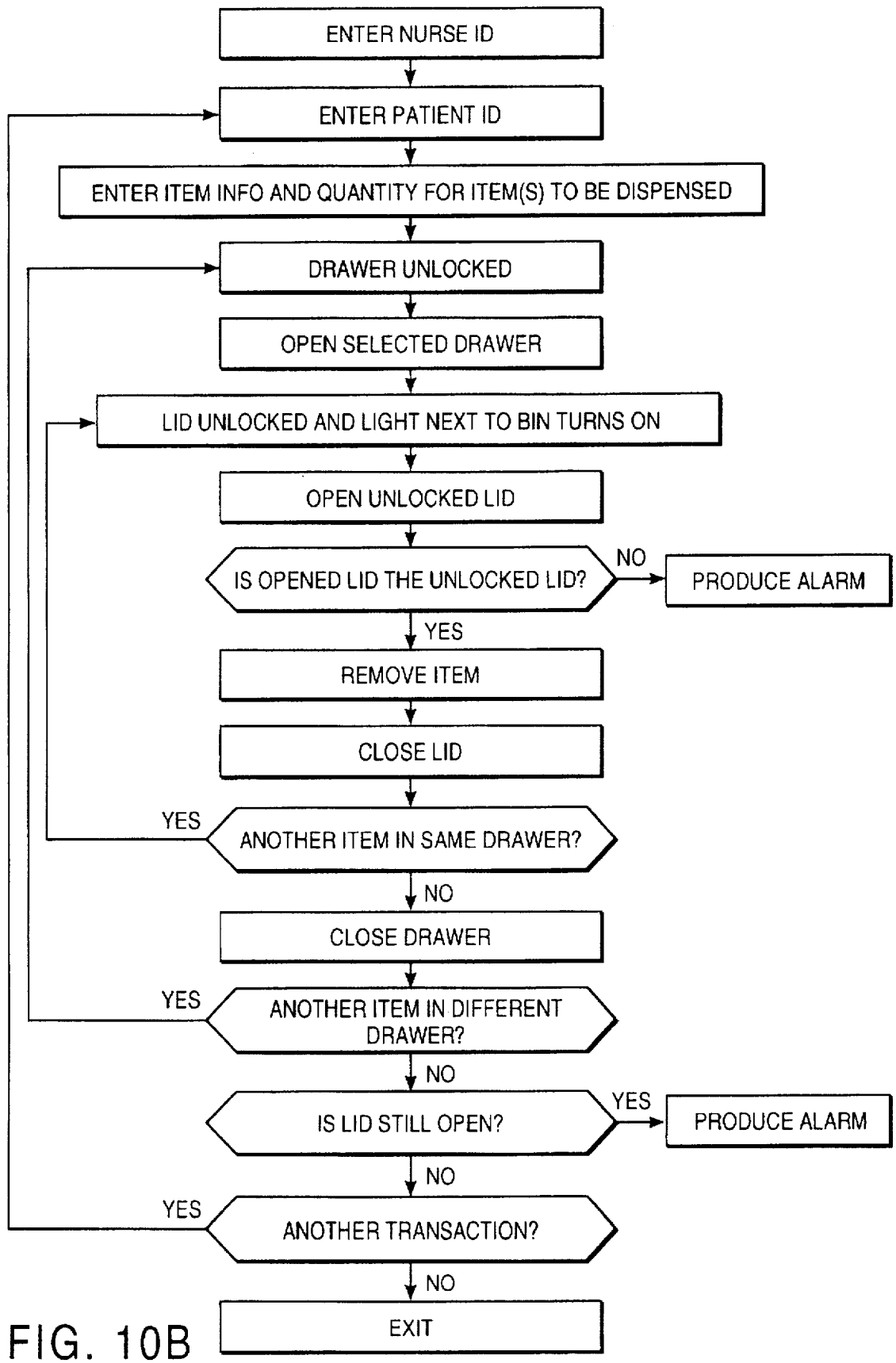
FIGS. 10B–10D are flowcharts of alternative methods for dispensing pharmaceutical items from the dispensing unit of FIG. 10 according to the present invention.
Figure 10C:
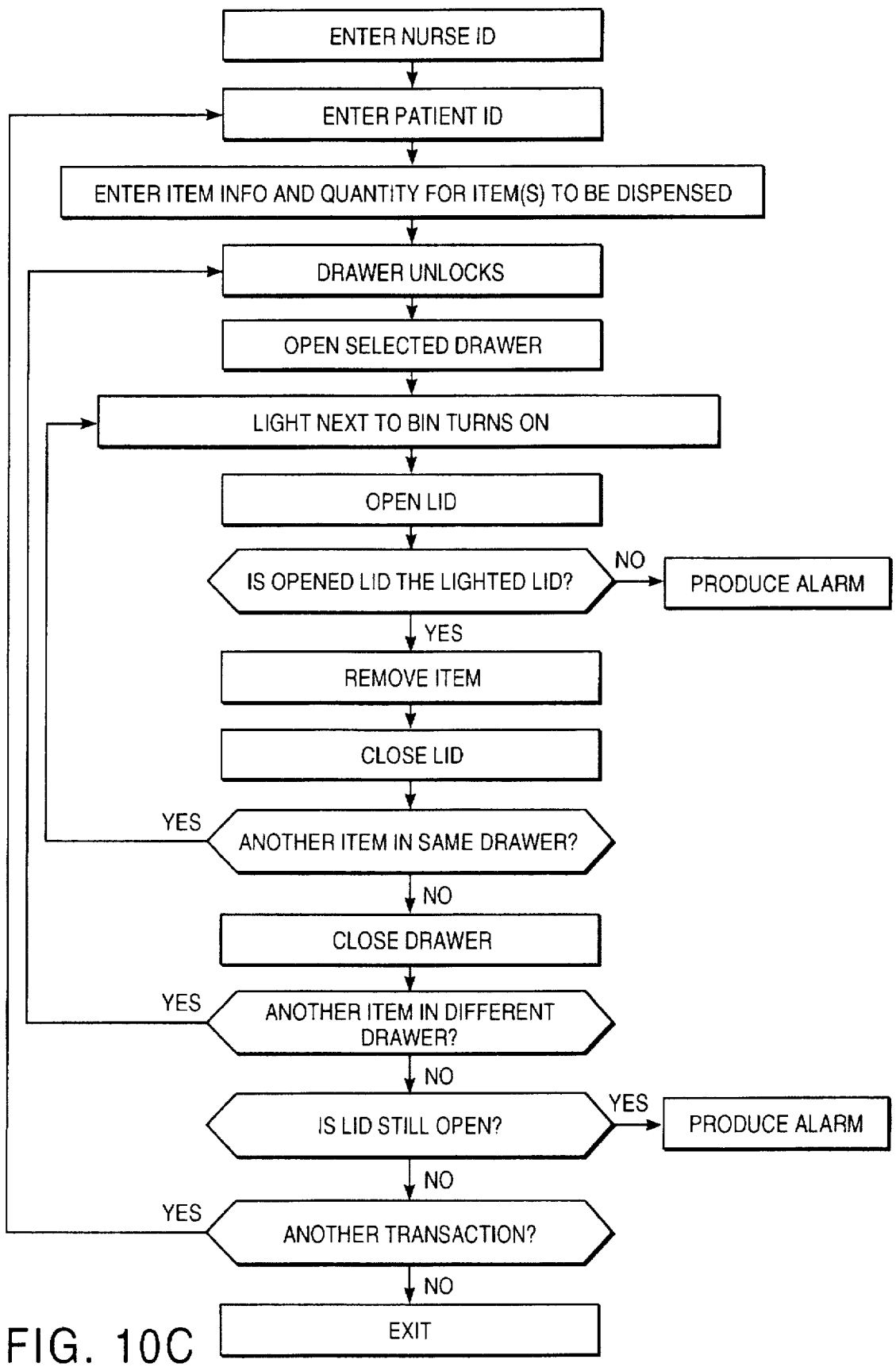
Figure 10D:
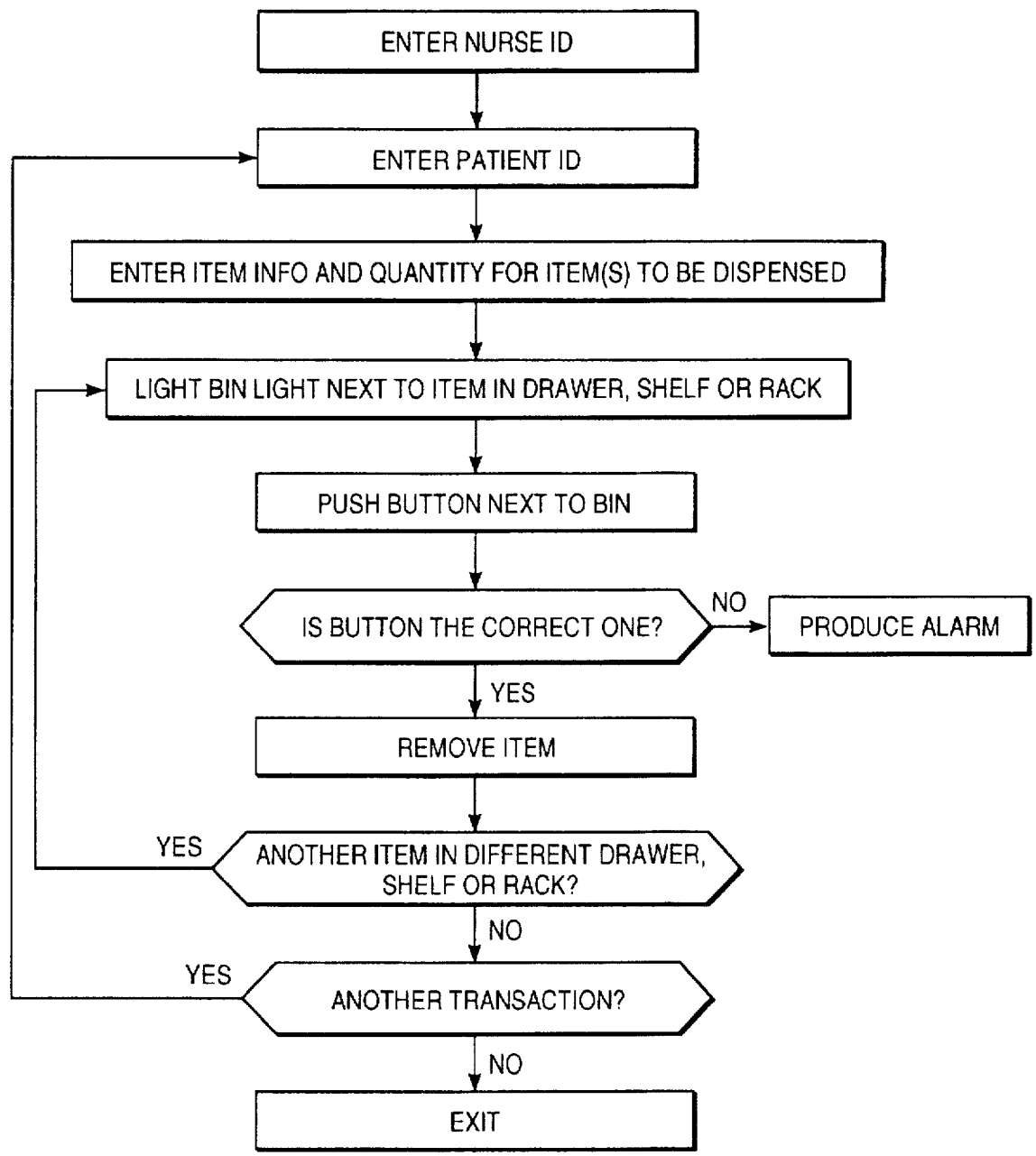

FIG. 10B illustrates a method for providing highest level of security when item and quantity information has been pre-selected, i.e. directly entered into the processor 210 prior to access and removal. After such information is entered into the processor 210, a first drawer 212 unlocks having a first one of the pre-selected items (assuming the nurse may have access to that drawer). Optionally, the button 222 may light to indicate the unlocked drawer. The drawer 212 is then retracted and the button 220 adjacent the bin having the first item is lighted to assist the nurse in locating the item. All of the lids 218 will be locked except for the lid covering the bin 216 having the item which will unlock after receiving a signal from the processor 210 (based on the pre-entered item information). The lid 218 is then opened and the item (or items) is removed. In the event that the nurse attempts to open another (unlocked) lid, an alarm is produced.

Following removal, the lid 218 is closed. If another pre-selected item is held within the retracted drawer 212, the button 220 adjacent another bin 216 having the next item is lighted. This bin is then unlocked, and the item is removed from that bin as previously described. After all items have been removed from the retracted drawer, the drawer is closed. If other preselected items are in other drawers, they will each in turn unlock as previously described. In the event that a lid is open when a drawer 212 is closed, an alarm will sound to remind the nurse to close the lid.

Recordation of item removal is accomplished by sensing when each lid is opened. Since the processor is already provided with information regarding the items (including quantity) to be removed, such lid sensing information can be used to confirm that the pre-selected items have actually been removed (and hence used to produce a record of item removal).

In some cases, a given bin will not have a sufficient inventory of pre-selected items. In this case, the nurse will remove all items (of a single type) from a bin with a lighted button 220. When the lid 218 is closed, the processor 210 will know how many more items of the same type are still needed. The processor 210 will then send a signal to light the button 220 adjacent another bin 216 having the same type of items so that the pre-selected quantity can be dispensed.

Before granting access to certain bins, the processor 210 may be configured to require the presence of a witness. In that event, a witness will be required to enter witness identification information into the processor 210 before access to the desired bin will be granted.

A method for dispensing items with a lower level of security is illustrated in FIG. 10C. The method of FIG. 10C is essentially identical to that of FIG. 10B except that the lids 216 are not locked. However, if a nurse attempts to access a bin 216 for which the button 220 is not lighted, an alarm will be produced. Alternatively, instead of producing an alarm, the nurse can optionally be prompted to enter item identification information into the processor 210 for additional items that were not originally selected.

A method for dispensing items with still a lower level of security is illustrated in FIG. 10D. With the method of FIG. 10D, the items do not need to be held in a bin with a lid. Optionally, the items may even be held on a rack or a shelf. After item and quantity information have been entered into the processor 210, the button 220 adjacent the bin 216 (or rack or shelf) having a first pre-selected item will be lighted. The nurse will then touch the button 220 to confirm that access to the that bin has been obtained. If an incorrect button is selected, an alarm will be produced. Upon touching the correct button 220, the nurse then removes the item (or items). If another type of item has been pre-selected, the button 220 adjacent the bin 216 having the next item will be lighted. After all items have been removed from the first drawer, the drawer is closed. If other preselected items are in other drawers, the nurse will in turn be directed to each drawer and each bin as previously described.

Restocking of the drawers may be accomplished in essentially the same manner as described with the dispensing unit of FIG. 1 and as described in copending U.S. application Ser. No. 08/095,619, previously incorporated herein by reference. Alternatively, to restock drawers with items needing heightened security, only the particular drawer 212 and bins 216 to be restocked will be unlocked. All remaining bins 216 will be locked throughout the restocking process.

In an alternative restocking procedure, a list of items and associated quantities that are to be restocked may be entered into the processor 210 prior to restocking. Preferably, the processor 210 will be in communication with a central processor (not shown) which will regularly monitor the inventory levels for each dispensing unit within the hospital. When ready for restocking, the central processor will send the list of items and quantities that are to be restocked to the processor 210. The buttons 220 may then be lighted to guide the restock person through the restocking procedure. Each button may be pressed once to produce a message indicating how many items are to be restocked in a given bin 216. After the restock person has filled a bin 216, the touch-sensitive button 220 adjacent the restocked bin 216 may be touched once to confirm that the receptacle has been restocked with items corresponding to the pre-entered information. If the restock person wishes to restock an item or a quantity that is different from the pre-entered information, such information may be manually entered into the processor 210 during the restocking process.

As previously mentioned, each of the bins 216 may be provided with a sensor to detect when the lid 218 covering the bin 216 has been at least partially removed when accessing the bin 216. In this way, heightened security can be provided to the items since the nurse will know that each time a lid 218 is opened a record of access will be produced. If the nurse opens one of the lids 218 and does not press the corresponding bin button 220 to record a transfer, a discrepancy between the access record and the removal record will result, thereby requiring the nurse to account for the discrepancy. In the case where item and quantity information are pre-selected, the button 220 may not be needed since the lid sensor may be used to produce a record of item removal.

Figure 11:
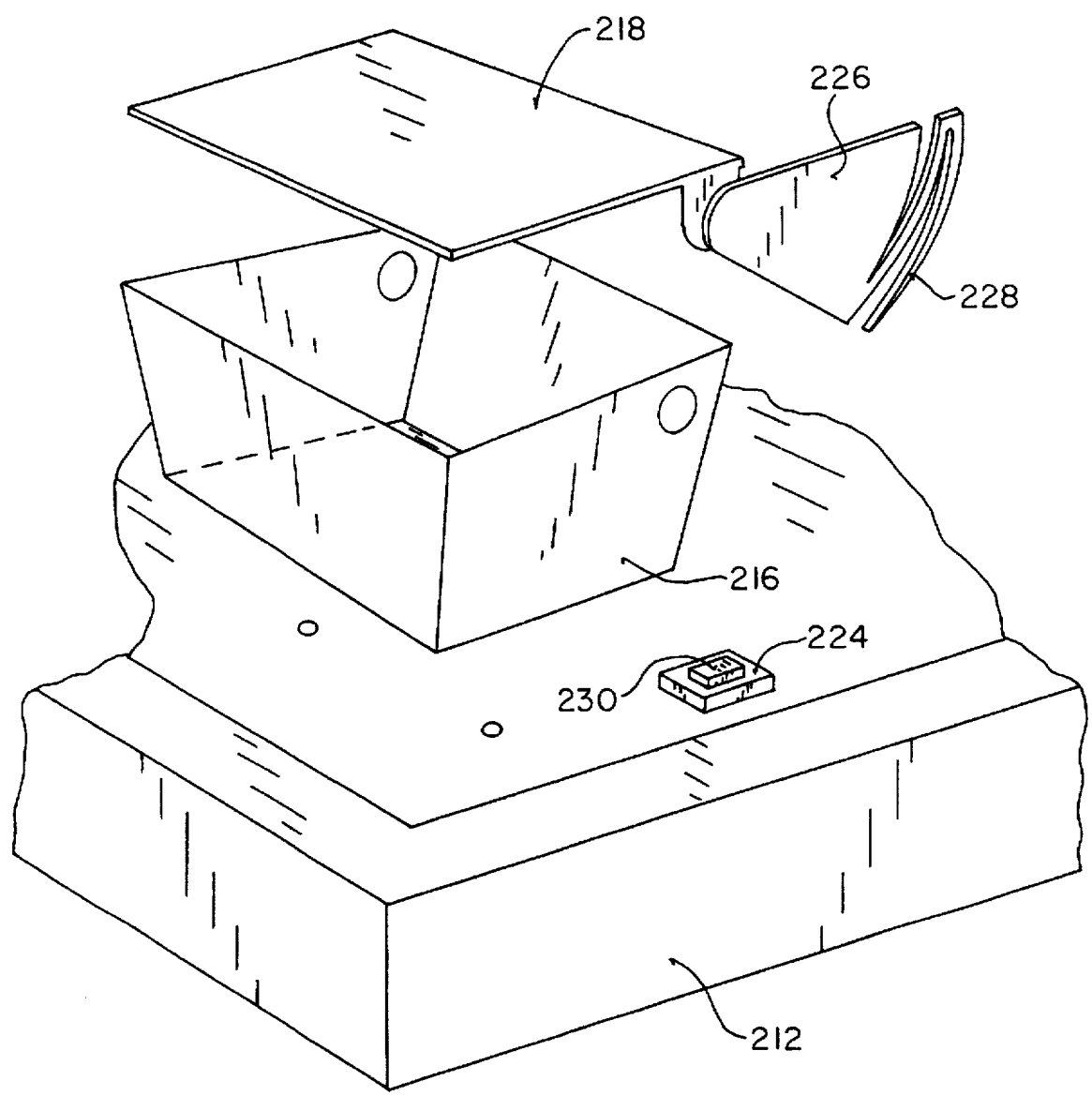
FIG. 11 is an exploded perspective view of an exemplary bin for holding pharmaceutical items according to the present invention.
Figure 12:
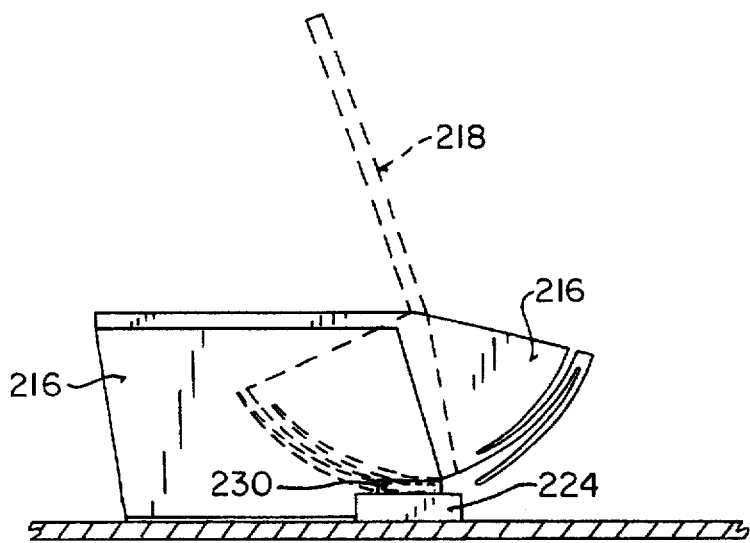
FIG. 12 is a side view of the bin of FIG. 11 showing operation of a sensor used to detect access to the bin.

A variety of sensors may be employed to detect removal of the lid 218 so that a signal may be sent to the processor 210 to produce an access record (or removal record) for each of the bins 216. One exemplary sensor 224 is illustrated in FIGS. 11 and 12. The sensor 224 is an electro-mechanical sensor that is depressed by an arm 226 on the lid 218. The lid 218 is pivotally attached to the bin 216 so that as the lid 218 is lifted, the arm 226 is rotated toward the sensor 224. Optionally, a strain relief portion 228 may be provided on the arm to prevent damage to the arm 226 or the sensor 224. As best shown in FIG. 12, the arm 226 comes in contact with the sensor 224 as the lid 218 is lifted. In turn, the contact of the arm 226 with the sensor 224 causes a switch 230 on the sensor 224 to depress and make an electrical contact within the sensor 224. Upon contact, a signal is sent to the processor 210 to produce a record of access (or removal).

Figure 13:
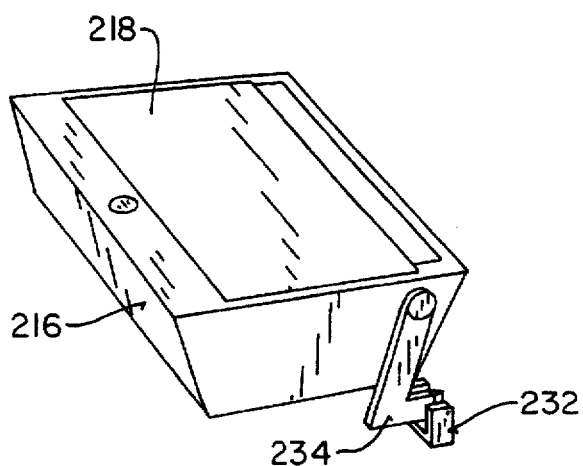
FIG. 13 is a perspective view of an alternative lid and sensor for a pharmaceutical bin according to the present invention.
Figure 14:
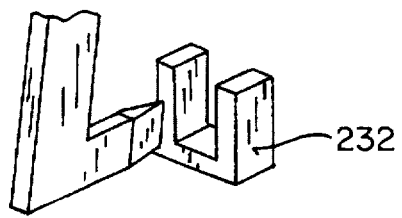
FIG. 14 is a more detailed view of the sensor of FIG. 13.

Referring to FIGS. 13 and 14, an alternative embodiment of a sensor 232 will be described. The sensor 232 comprises an IR pair detector. Attached to the lid 218 is an arm 234 which is received in the sensor 232 when the lid 218 is closed. As best shown in FIG. 14, as the lid 218 is opened the arm 234 pivots and slides from the sensor 232 to break an electrical circuit. The opening of the circuit is detected and a signal is sent to the processor 210 to record an access to the bin 216 (or to produce a record of removal).

Figure 15:
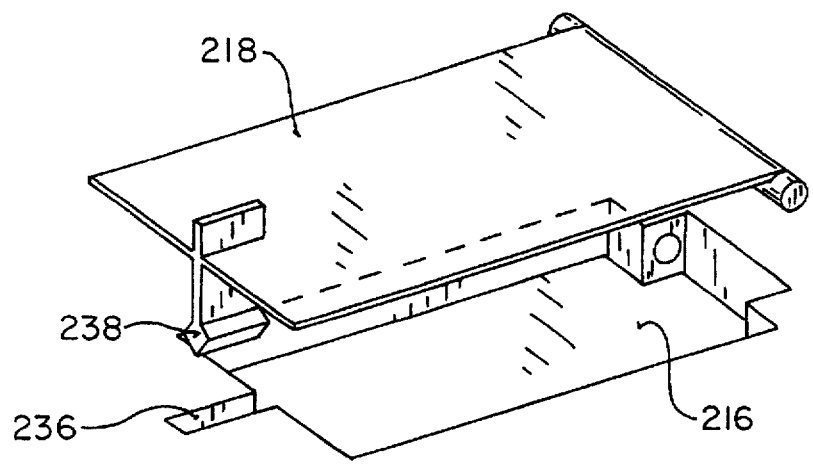
FIG. 15 is a perspective view of an alternative bin arrangement according to the present invention.
Figure 16:
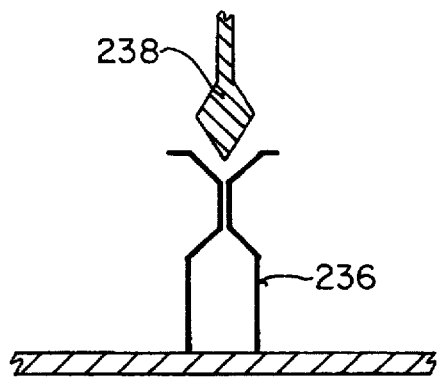
FIGS. 16 and 17 illustrate operation of a sensor that is used to detect access to the bin of FIG. 15.
Figure 17:
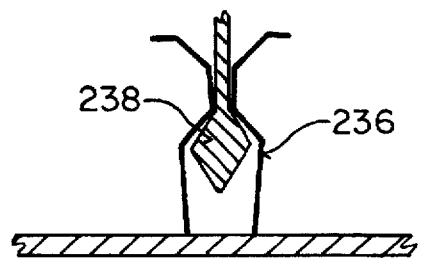

A further alternative embodiment of a sensor 236 for the bin 216 is shown in FIGS. 15–17. The sensor 236 comprises a metallic spring clip that is part of an electrical circuit. The lid 218 includes a tab 238 that is removed from the sensor 236 when the lid 218 is open as best shown in FIG. 16. When the lid 218 is closed, the tab 238 separates the spring clip 236 to close the circuit. As the lid 218 is opened, the clip 236 closes and the circuit is opened. When the circuit is opened, current flow through the circuit may be detected and a signal sent to the processor 210 to record access to the bin 216 (or to produce a record of removal).

Figure 18:
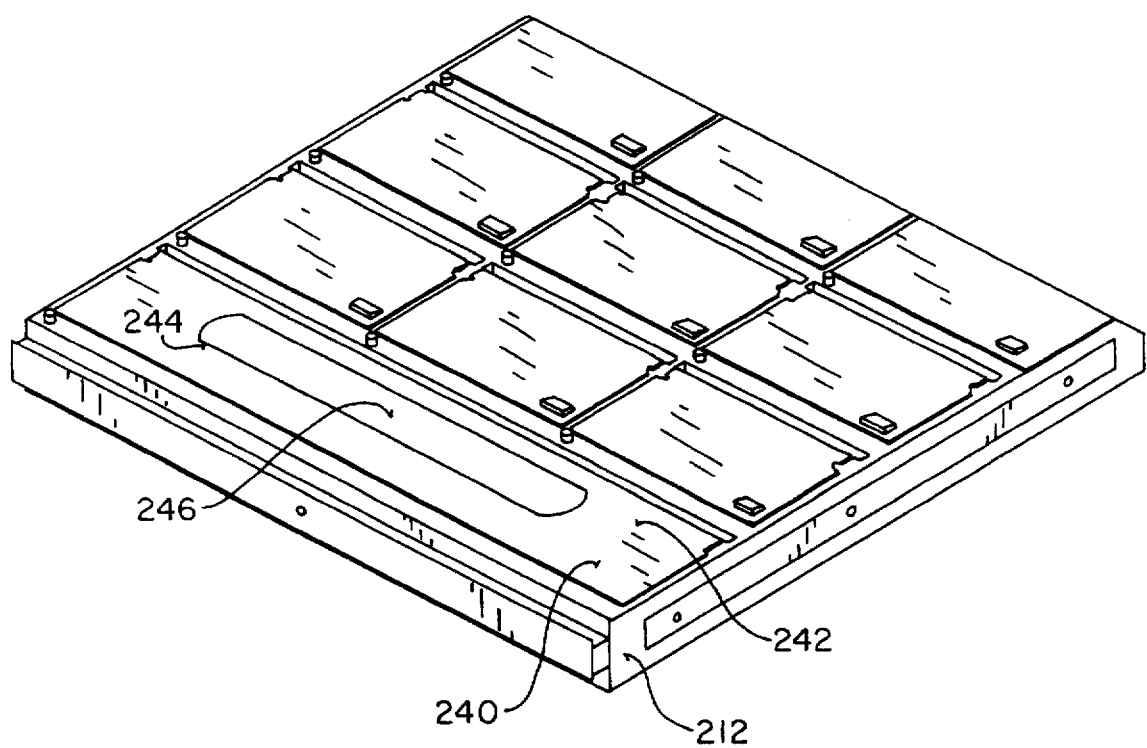
FIG. 18 illustrates an alternative embodiment of a drawer for the dispensing unit of FIG. 10 having a wastage container for receiving wasted items according to the present invention.

Referring to FIG. 18, one embodiment of the drawer 212 having a waste receptacle 240 will be described. The waste receptacle 240 is provided to receive items that have previously been dispensed but for some reason cannot be returned to its original storage location (such as if the item has been only partially used or has been contaminated). In such cases, it is desirable to return the item so that the patient's bill may be credited and also so that the nurse may have evidence of the item's return which may subsequently be needed to explain the removal of a replacement item. The waste receptacle 240 is covered by a lid 242 having an elongate slot 244. The slot 244 is preferably covered by a one-way door 246 so that items may be introduced into the receptacle 240 through the one-way door 246 but cannot be removed once they are placed therein. The lid 242 will preferably be locked so that access to the receptacle 240 can only be gained by authorized personnel once appropriate identification information has been input into the processor 210.

Figure 18A:
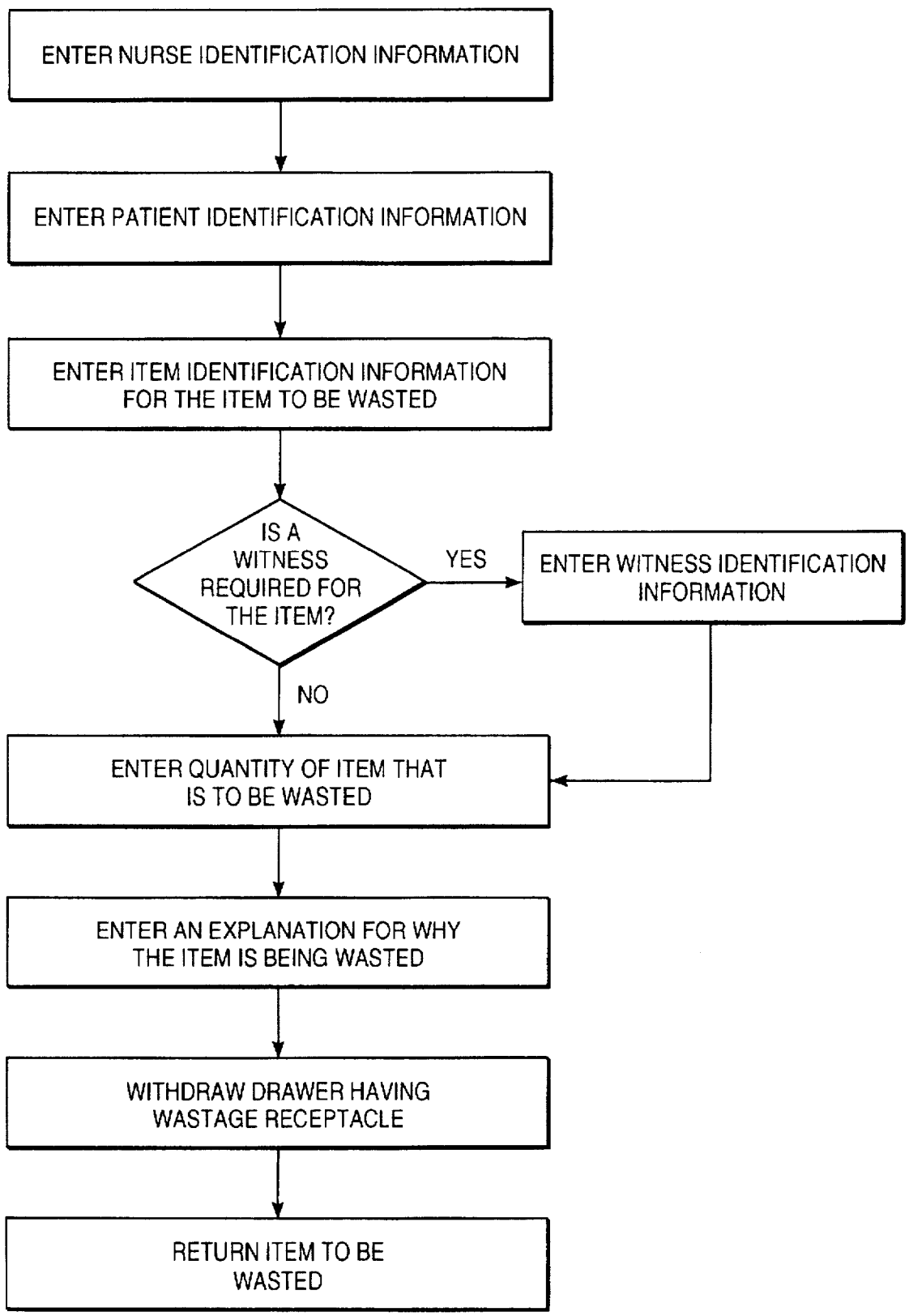
FIG. 18A is a flowchart of an exemplary method for wasting previously dispensed items according to the present invention.

Illustrated in FIG. 18A is an exemplary method for wasting a previously dispensed item into the waste receptacle 240. Initially, the nurse returning the item enters nurse identification information into the processor 210. The nurse will also enter information into the processor 210 identifying the patient for whom the item was originally dispensed so that the patient's account may be credited. The nurse will further enter item identification information into the processor 210 identifying the item to be wasted. With some items, a witness will be required during wastage. In such an event, the processor will prompt the nurse to have a witness enter their identification information into the processor 210. The processor 210 will also prompt the nurse to enter the quantity of the item that is to be wasted along with an explanation of why the item is to be wasted. After such information has been input into the processor 210, the nurse withdraws the drawer 212 having the waste receptacle 240 and places the item to be wasted in the slot 244.

When dispensing pharmaceutical items, it is often desirable to store only a single item in each of the receptacles, often referred to as single dose dispensing. By providing only one item in each of the receptacles, records containing access information to the receptacles and transfer information of items from the receptacles can more easily be correlated. Single dose dispensing is provided in the present invention by providing a sensor for each of the receptacles so that as each receptacle is accessed, a record of the access is produced. In the case where item and quantity information are pre-entered, the record of access may also be employed to produced a record of removal. Each receptacle may optionally be provided with an associated touch-sensitive button for recording transfer information as an item is removed from each receptacle. Since only one item is held in each receptacle, if the access report and the transfer report do not correlate, the nurse responsible for the discrepancy may more easily be identified.

Figure 19:
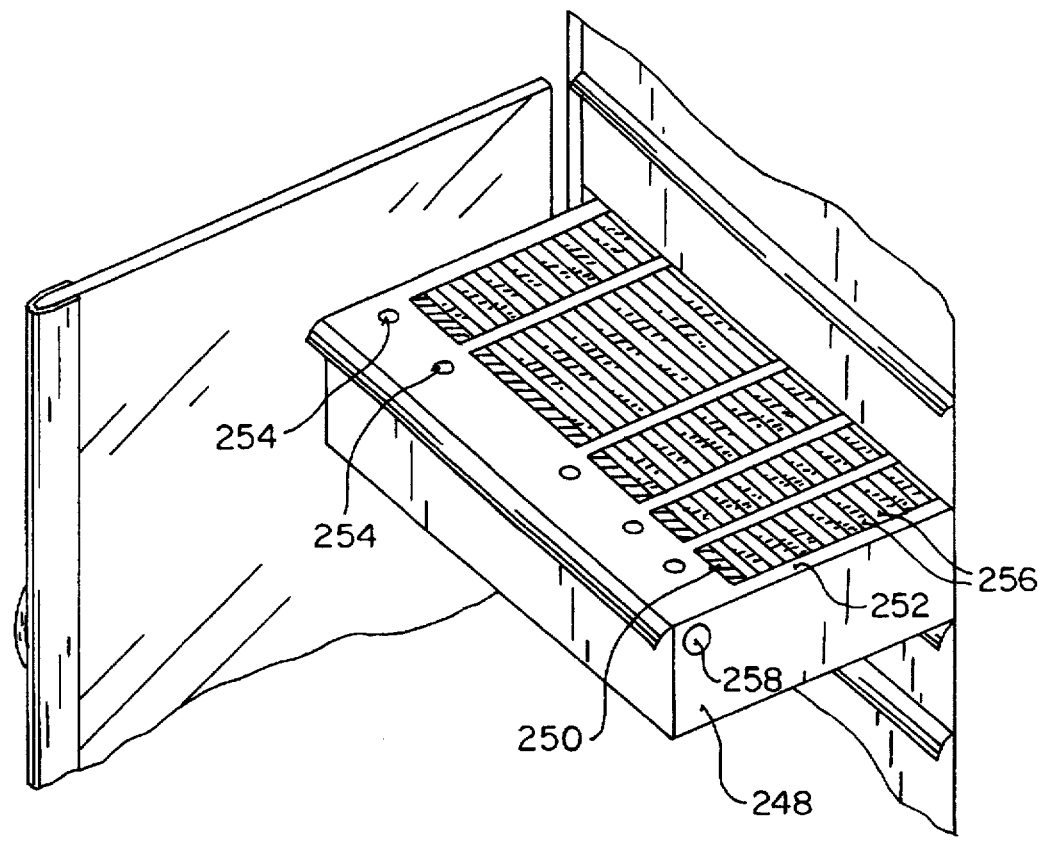
FIG. 19 illustrates a further alternative embodiment of a drawer for the dispensing unit of FIG. 10 having a plurality of receptacles for holding single doses of pharmaceutical items according to the present invention.
Figure 20:
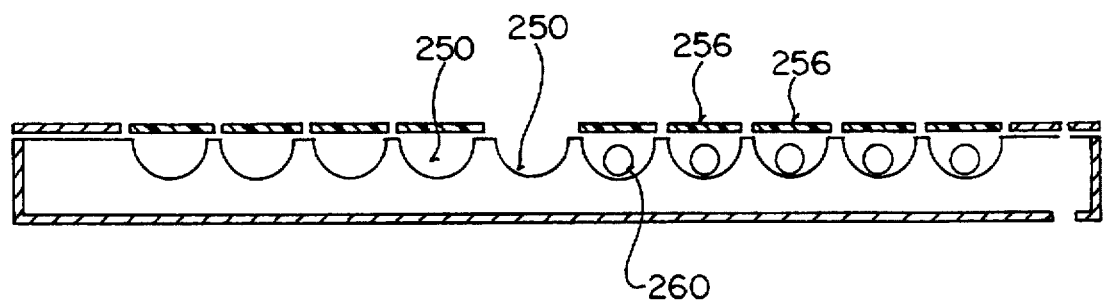
FIG. 20 is a cross-sectional view of the drawer of FIG. 19.

An exemplary drawer 248 that is configured to dispense items in single doses is illustrated in FIGS. 19 and 20. The drawer 248 may be integrated into the dispensing unit 200 in the pharmaceutical zone 204 in a manner similar to the drawers 212. The drawer 248 includes a plurality of receptacles 250. The receptacles 250 may vary in size, and are preferably aligned in rows. As described in greater detail hereinafter, the receptacles 250 are slidably held behind a cover 252 which is removable from the drawer 248 to provide access to all of the receptacles 250 during restocking. Associated with each row of receptacles 250 is a touch-sensitive receptacle button 254. The buttons 254 operate essentially identical to the bin buttons 220 to record transfer of items to or from the receptacles 250 as previously described. The buttons 254 may also be used to direct a nurse to the proper receptacle 250.

A plurality of lids 256 are provided to cover the receptacles 250. The lids 256 are slidably received within the cover 252 and can be axially translated along their respective rows. Each row of receptacles 250 will have all but one of its receptacles covered by a lid 256. In this way, only one receptacle 250 in each of the rows can be accessed at a time. To access an item 260, the lid 256 covering that item 260 will be slid from its receptacle 250 until it covers an adjacent receptacle 250 that does not have a lid 256. Optionally, a manual lock 258 will be provided to lock the cover 250 to the drawer 248 so that access to all of the receptacles 250 (such as when restocking) may only be afforded when the lock 258 is opened.

Figure 21:
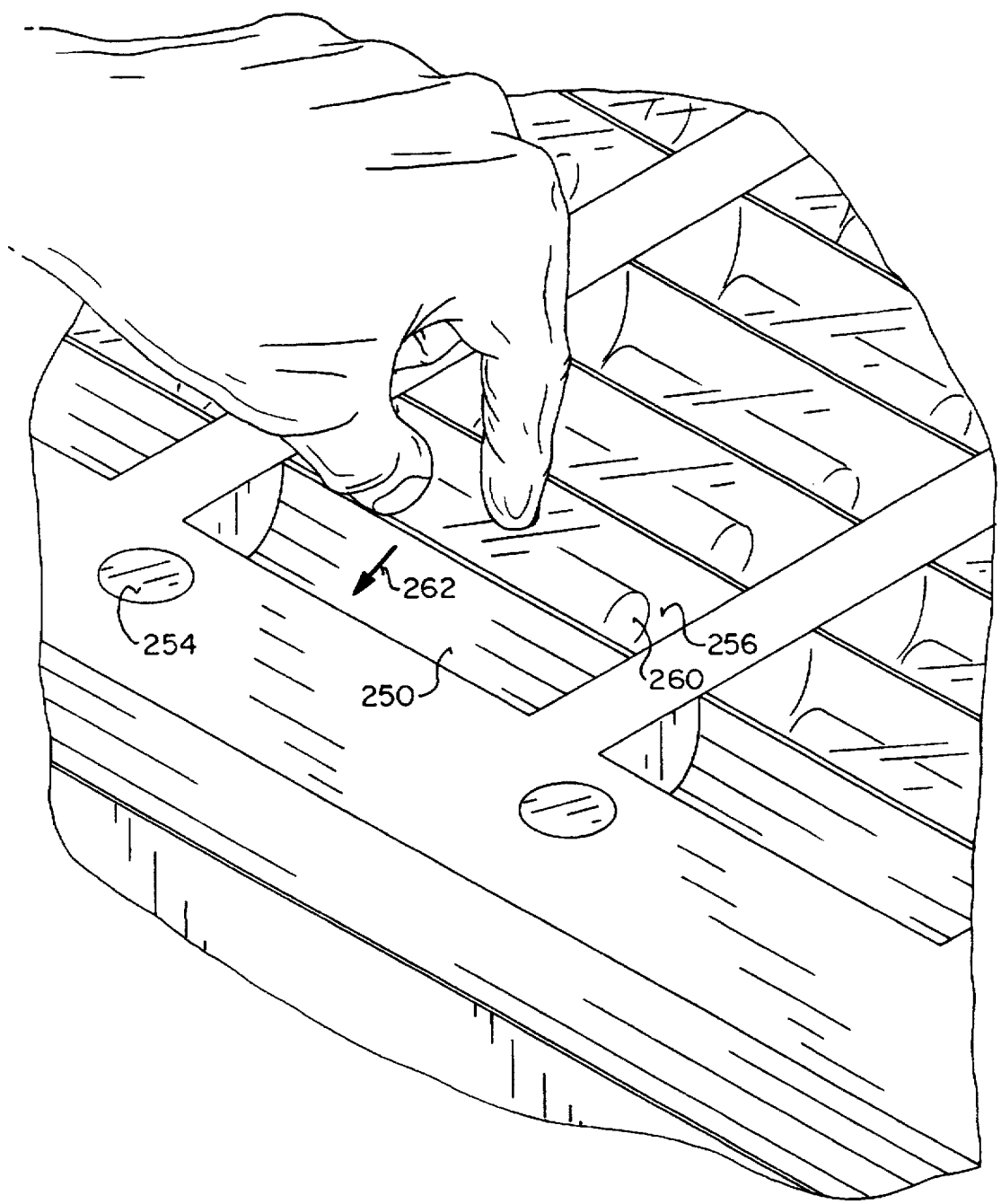
FIGS. 21 and 22 illustrate an exemplary method for removing items from the drawer of FIG. 19.
Figure 22:
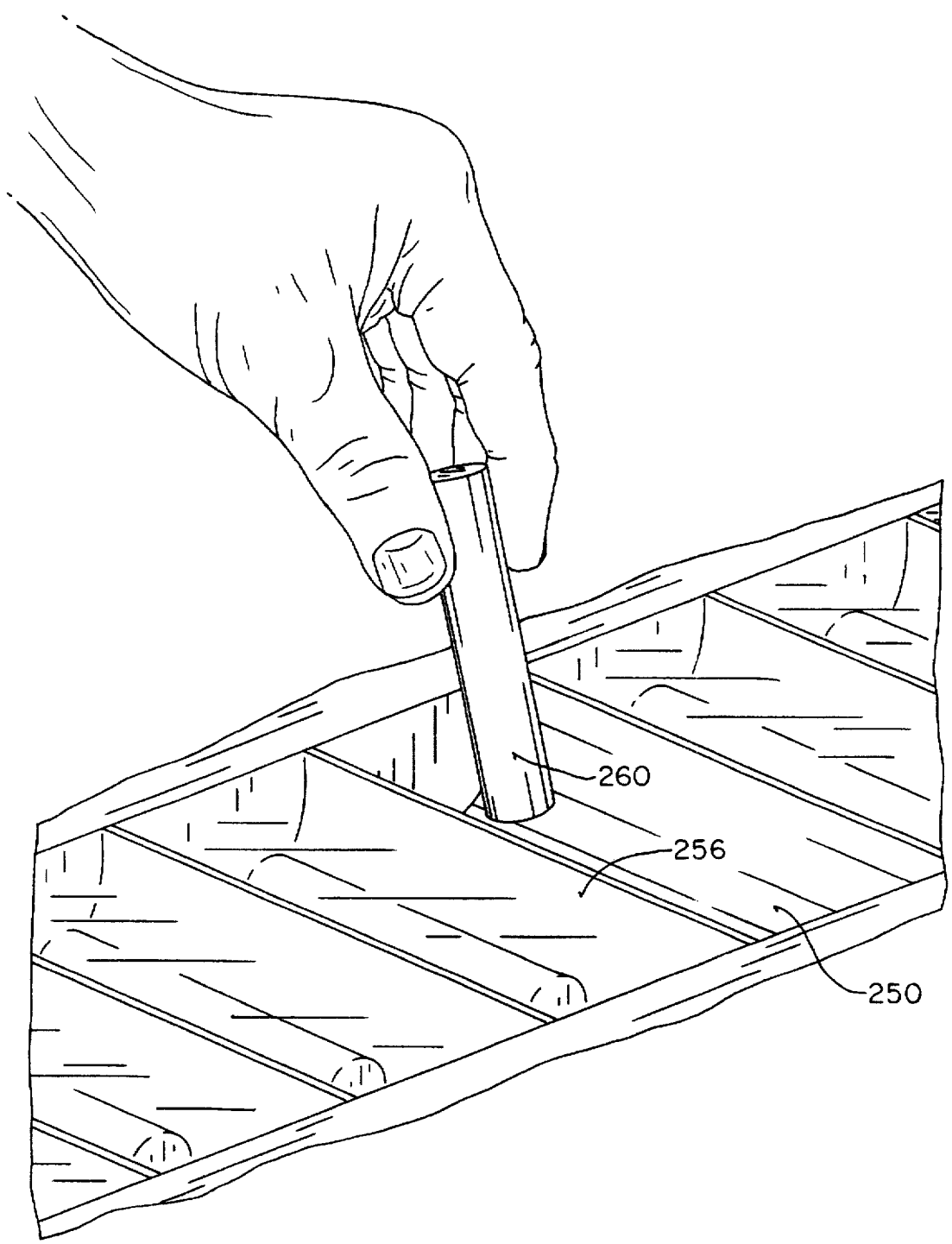

Referring to FIGS. 21 and 22, an exemplary method for removing one of the items 260 from one of the receptacles 250 will be described. After nurse and patient identification information have been entered and the drawer 248 is accessed as previously described, the nurse slides the lid 256 in the direction of arrow 262 to cover the adjacent (open) receptacle 250 and to expose item 260. The nurse then lifts the item 260 from the receptacle 250 as illustrated in FIG. 22. The nurse then touches the touch-sensitive receptacle button 254 in the row having the item 260 to record its transaction. As the lid 256 is translated from the receptacle 250, the removal of the lid 256 is sensed and is stored in the processor for later comparison. Alternatively, item and quantity information may be entered into the processor before a receptacle is accessed so that removal of a lid 256 will produce a record of item removal, thereby eliminating the need to push to button 254. Further, access to certain receptacles can be controlled (e.g. with a lock) based on the pre-entered item identification information.

Removal of the lid 256 from the receptacle 250 may be sensed with a variety of mechanisms such as optical sensors, electromechanical sensors, and the like. One exemplary optical sensor 264 is illustrated in FIG. 23. The sensor 264 comprises a light source 265 and a photodetector 267. As the lid 256 is translated from the receptacle 250, light from the light source 265 directly impinges on the photodetector 267 to produce a record of the lid's removal.

An alternative sensor 266 is illustrated in FIGS. 24 and 25. The sensor 266 comprises a pair of electrically conductive leads 268 that are biased together to close an electrical circuit. Conveniently, the leads 268 also form a track for the lid 256. When the lid 256 is inserted between the leads 268, the leads 268 are separated from each other and the circuit is broken. To access the receptacles 250, the lid 256 is slid from the leads 268 to close the circuit. The closing of the circuit will then be detected and used to send a signal to the processor 210 indicating access to the receptacle 250.

Referring to FIG. 26, an alternative sensor 270 will be described. The sensor 270 is constructed in a manner similar to the sensor 266 except that the sensor 270 is vertically oriented. With this configuration, each of the lids 256 will be provided with a pair vertical walls 272, with one of the walls 272 being received within the sensor 270 to open the electrical circuit. When the lid 256 is slid from the receptacle 250, the wall 272 is removed from the sensor 270 to close the circuit so that a signal may be detected.

Figure 27:
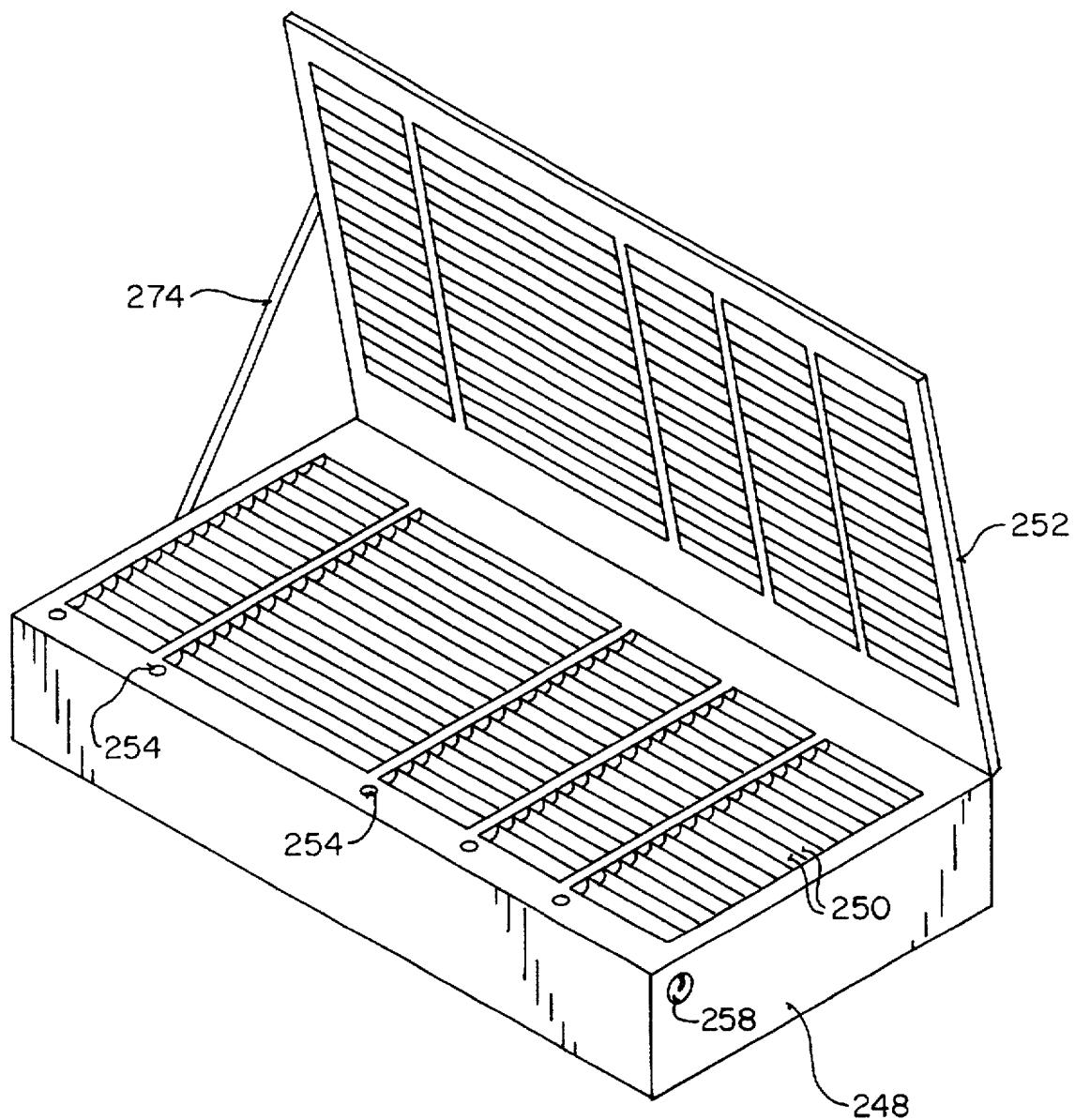
FIG. 27 is a perspective view of the drawer of FIG. 19 having the cover lifted to simultaneously expose all the receptacles for restocking according to the present invention.
Figure 28:
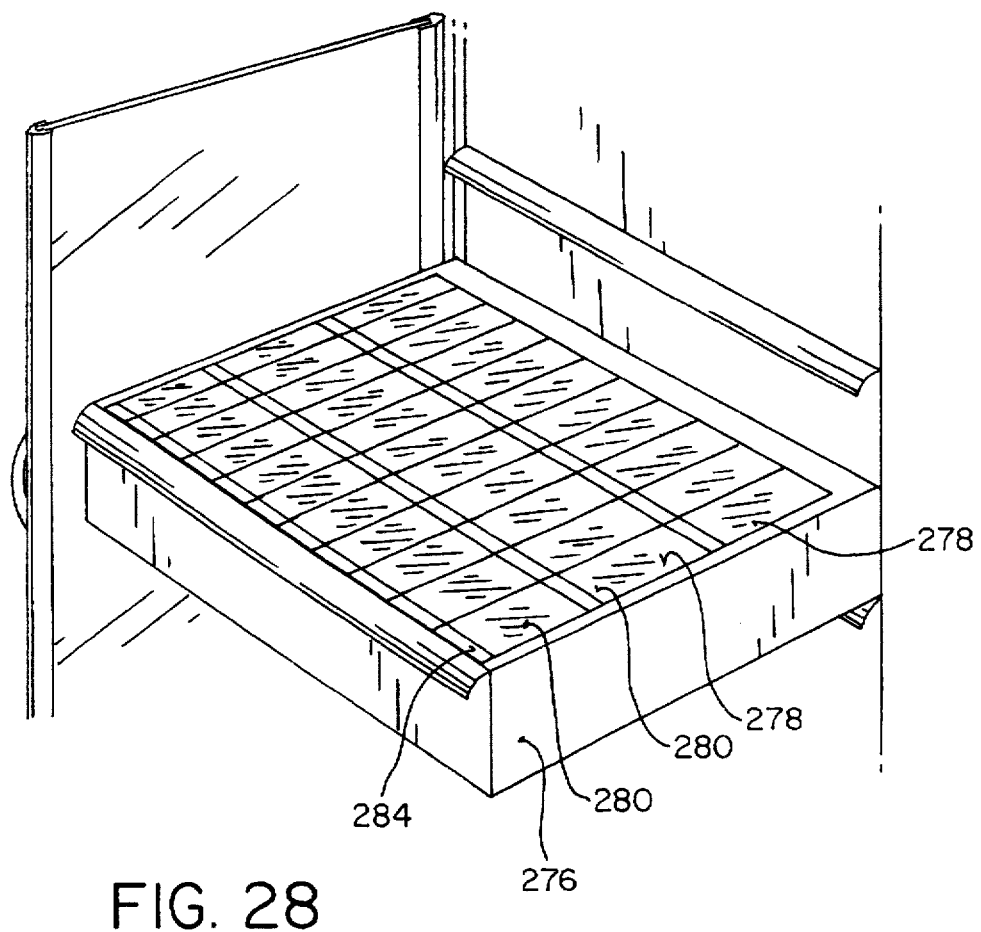
FIG. 28 is a perspective view of an alternative drawer for the dispensing unit of FIG. 10.

Referring to FIG. 27, removal of the cover 252 to expose the receptacles 250 during restocking will be described. For restocking, the dispensing unit 200 is placed in restocking mode and the drawer 248 is accessed as previously described. The technician then inserts a key into the lock 258 to unlock the cover 252. The cover 252 is then raised and is held open by an arm 274. When the cover 252 is raised, all of the receptacles 250 are available for access so that the technician can rapidly fill each of the receptacles 250. Recordation of the transfer may be accomplished by pressing the touch-sensitive receptacle button 254 the number of times for the number of items replaced into each row of receptacles 250. After restocking, the lid 252 is closed and locked, and the drawer 248 is then closed. In an alternative restocking procedure, the processor may be provided with a list of items that are to be restocked. Once such items have been restocked, the restock person may touch the button 254 once to confirm that restocking has occurred.

Figure 29:
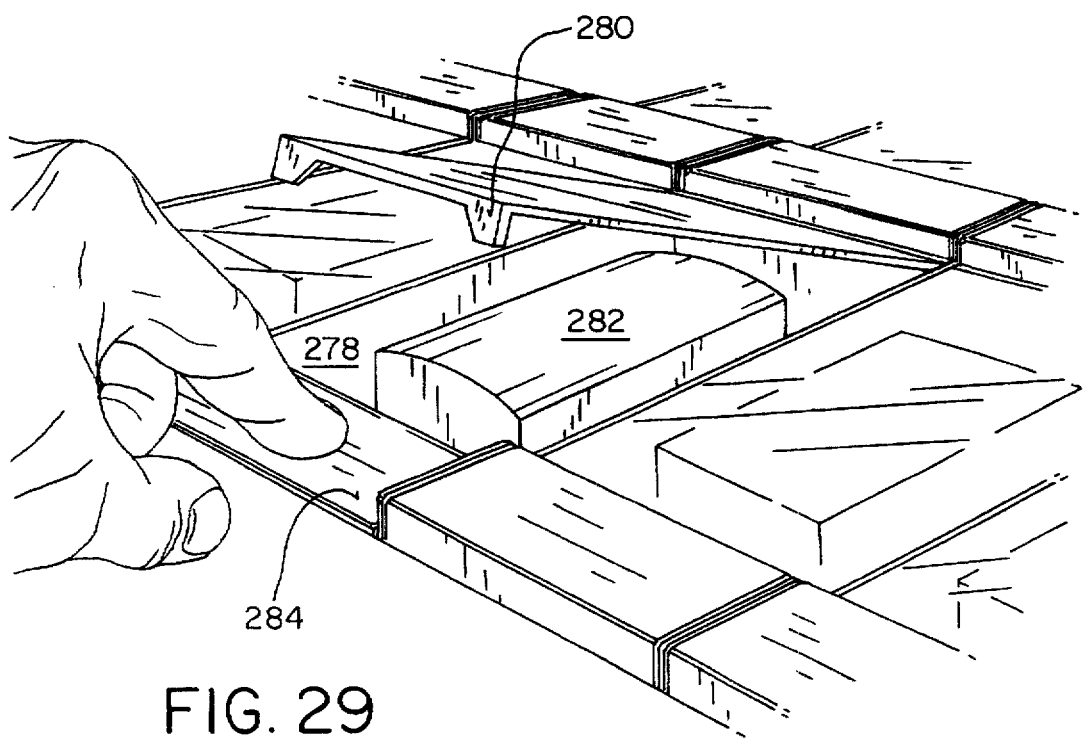
FIG. 29 illustrates an exemplary method for gaining access to a bin of the drawer of FIG. 28.

Referring FIGS. 28–31, an alternative embodiment of a drawer 276 for single dose dispensing will be described. The drawer 276 may be incorporated into the dispensing unit 200 in the pharmaceutical zone 204 in a manner similar to drawers 212 or 248 as previously described. The drawer 276 includes a plurality of receptacles 278 that are each covered by a lid 280. As best shown in FIG. 29, each lid 280 is pivotally attached over its associated receptacle 278. The receptacles 278 are sized to receive a single pharmaceutical item such as a drug 282 (see FIG. 29). To gain access to the receptacles 278, a release button 284 that is adjacent each receptacle 278 is depressed as shown in FIG. 29. The lid 280 is spring loaded so that upon depression of the release button 284, the lid 280 is unlatched and swings open. Depression of the release button 284 also produces a record of access to the receptacle 278.

Figure 30:
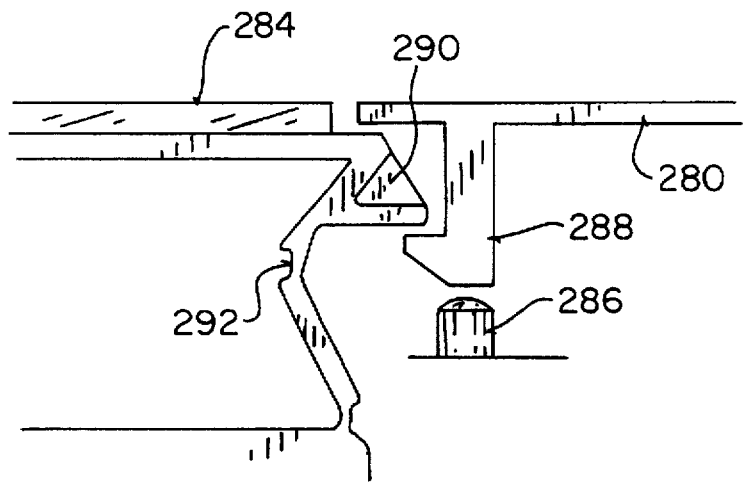
FIGS. 30 and 31 are side views of a lid and sensor for the drawer of FIG. 28.
Figure 31:
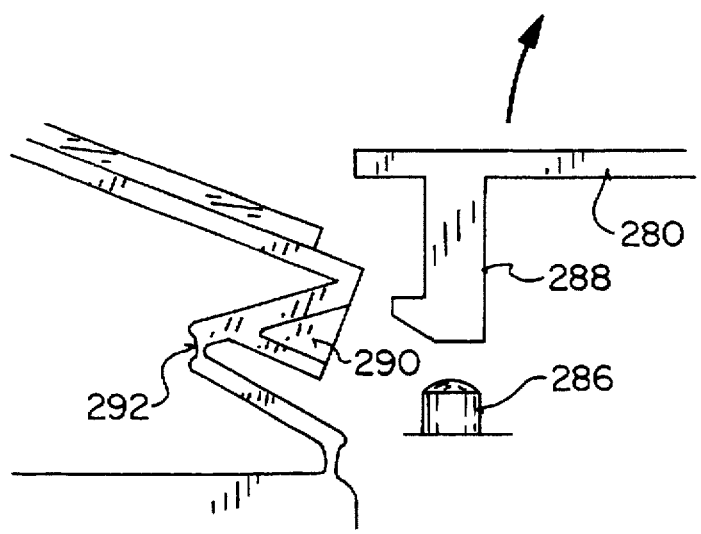

As best shown in FIGS. 30 and 31, associated with each lid 280 is a sensor 286 which is activated by an arm 288 on the lid 280 when the button 284 is depressed. Arm 288 is also configured to engage a latch 290 on the release button 284 when the lid 280 is in a closed position. The latch 290 holds the lid 280 securely over the receptacle 278 to prevent access to the receptacle 278 until the release button 284 is depressed. As the button 284 is depressed, the latch 290 buckles inward about a hinge 292 and disengages the latch 290 from the arm 288. As the latch 290 moves downward and inward upon depression of the release button 284, the arm 288 is forced downward toward the sensor 286. The tolerance between the arm 288 and the sensor 286 is such that the arm 288 contacts the sensor 286 before the arm 288 is released from the latch 290. In this way, the sensor is able to detect when the button 284 is depressed and can send a signal to the processor 210 to indicate access to the receptacle 278. Optionally, a touch-sensitive button (not shown) similar to the button 254 on the drawer 248 can be provided for recording removal of the drug 282 from the receptacle 278 after the lid 280 has been opened. A record of removal can then be compared with the access record to determine any discrepancies as previously described. In a further alternative, the lids 280 may be provided with locks (not shown) which are in communication with the processor 210. Further, item identification information will be required to be entered into the processor 210 before a corresponding lid will be unlocked. In this way, access to certain receptacles 278 can be limited by the processor 210 to only receptacles having items from the pre-entered item identification information.

Referring to FIGS. 32–36, yet another alternative embodiment of a drawer 294 for single item dispensing will be described. The drawer 294 may be included in the dispensing unit 200 in the pharmaceutical zone 204 in a manner similar to the drawers 248 and 276 as previously described. The drawer 294 is provided with a plurality of enclosures 296 that are each covered by a lid 298. For convenience of discussion, the lid on the exposed enclosure 296 is shown removed. Within each enclosure 296 are three rollers 300, 302, and 304. As best shown in FIGS. 33–36, roller 302 is provided with two elongate slots 306 and 308, and roller 304 is provided with two elongate slots 310 and 312. Connected to the roller 300 is a motor (not shown) for rotating the roller 300. The roller 302 is in contact with the roller 300 so that upon rotation of the roller 300, the roller 302 will be rotated in the opposite direction. In a similar manner, the roller 304 is in contact with the roller 302 and will rotate in the direction of roller 300 when the roller 300 is rotated. The slots 306, 308, 310 and 312 are positioned so that upon each quarter turn of the roller 300 one of the slots will be exposed in the enclosure 296, as shown by the exposed slot 310 in FIG. 32.

A sensor (not shown) is provided for detecting when the lid 298 is opened. The sensor is in communication with the processor 210 so that when the lid 298 is opened a signal is sent from the processor 210 to the motor to rotate the roller 300 a quarter turn to expose a slot having an item. Each of the slots 306, 308, 310, and 312 are provided with a single pharmaceutical item so that upon each access to the enclosure 296 a single item will be available for removal. A touch-sensitive button 314 is provided for each enclosure 296 so that a record of removal can be produced each time an item is removed as previously described. In a further aspect, the sensor associated with each lid 298 will preferably be employed to send a signal to the processor 210 to produce a record of access to the enclosure 296 as previously described.

Alternatively, item identification information may be required to be entered into the processor before access will be given to a drawer or a receptacle. In this way, when removal of a lid 298 is sensed, a record of item removal may be produced, thereby eliminating the need to push to button 314. Further, access to certain receptacles can be controlled (e.g. by not rotating the roller 300) and will not be allowed unless item identification information has previously been entered into the processor.

Figure 32:
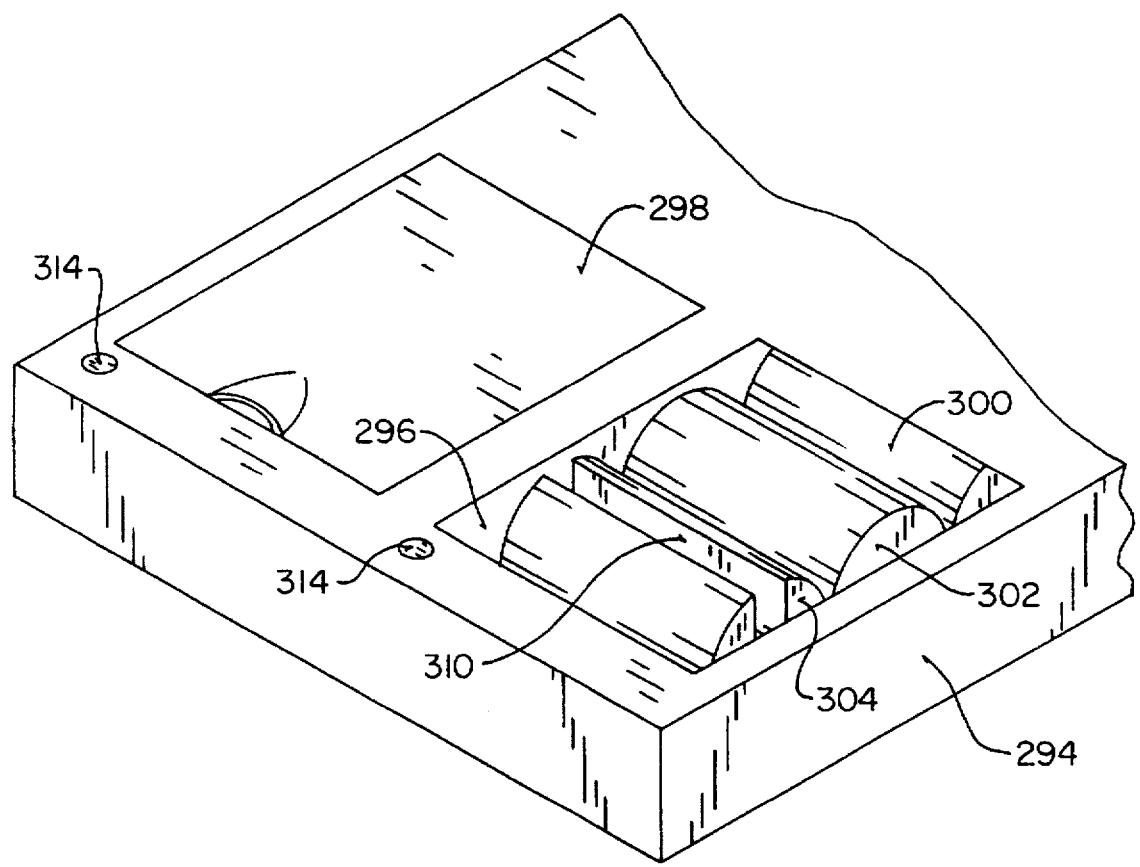
FIG. 32 is a perspective view of a further alternative embodiment of a drawer for the dispensing unit of FIG. 10 according to the present invention.
Figure 33:
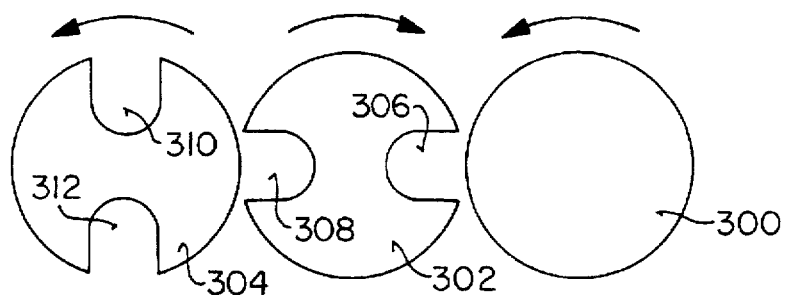
FIGS. 33-36 illustrate an exemplary method for gaining access to the receptacles of the drawer of FIG. 32.
Figure 34:
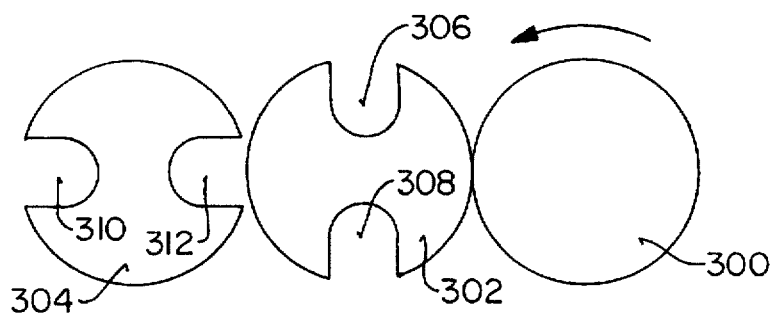
Figure 35:
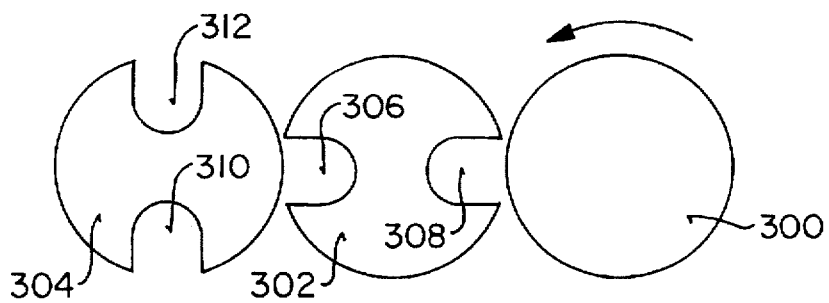
Figure 36:
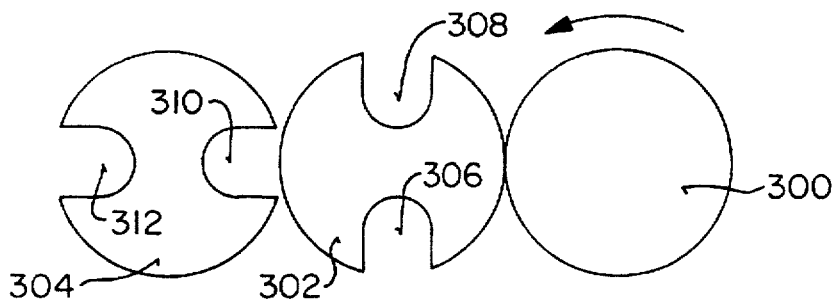

Referring to FIGS. 33–36, operation of the rollers 300, 302, and 304 will be described in greater detail. FIG. 33 illustrates the position of the rollers as shown in FIG. 32. As the lid 298 is opened, the roller 300 turns a quarter turn in a counter-clockwise direction, causing the roller 302 to rotate a quarter turn in a clockwise direction. In turn, the roller 304 is rotated a quarter turn in the counter-clockwise direction to place the slot 310 in a upward position where it is exposed in the enclosure 296. As shown in FIG. 34, the second time the lid 298 is opened, the roller 300 rotates another quarter turn in a counter-clockwise direction to place the slot 306 in an upward position where it is exposed in the enclosure 296. The position of the slots 306, 308, 310, and 312 when the lid 298 is opened the third time is shown in FIG. 35. As the roller 300 is rotated a quarter turn in the counter-clockwise direction, the slot 312 is placed in the upward position so that its item may be removed. As the lid 298 is opened the fourth time, the roller 300 turns a quarter turn in the counter-clockwise direction to place the slot 308 in the upward position, as shown in FIG. 36.

Although the enclosure 296 is shown with three rollers and four slots, other combinations of rollers and slots can be provided so that each enclosure 296 can hold more or less than four items.

Referring back to FIG. 10, additional features of the processor 210 will be described. Periodically, the items in the pharmaceutical zone 204 may need to be checked to determine if the items have expired or have been recalled. In such a case, an expiration/recall button 316 on the processor 210 may be selected so that access to the drawers 212 can be obtained. After pressing the button 316, the nurse selects the touch-sensitive drawer button 222 to open the selected drawer 212. Each time one of the lids 218 are opened, the processor 210 prompts the technician to enter the quantity of items removed. A record of removal is then produced so that an accurate inventory can be maintained in the pharmaceutical zone 204. In another aspect of the processor 210, item name aliases may be entered into the processor 210 so that a nurse may more easily be able to identify an item by either its brand name or its generic name.

The dispensing unit 200 may be connected to a local area network to place the processor 210 in communication with a central processor, as previously described, or with various other databases or processors. In one particular aspect, the processor 210 may be placed in communication with a variety of pharmaceutical databases, such as those having drug delivery information, dosage information, drug warning information, and the like. The processor 210 can alternatively be configured to only permit access to such information based on the nurse identification information that is initially entered into the processor 210. In this way, the processor 210 can regulate access to certain databases and information included on the local area network.

Placing the dispensing unit 200 on the local area network is further advantageous in that drug dispensing information can easily be downloaded. Usually, a variety of dispensing units that are similar to the dispensing unit 200 (and are in the same or in different hospitals) will be on the same network. In this way, drug consumption reports from a variety of hospitals can rapidly be generated to determine the types and quantities of drugs being dispensed.

The invention has been described in considerable detail for purposes of understanding. However, alternative embodiments of the invention will occur to those skilled in the art. Therefore, the above description should not be taken as limiting the scope of the invention. Instead, the scope of the invention should be determined chiefly with reference to the appended claims, along with the full scope of equivalence to which those claims are entitled.

What is claimed is:

1. A method for dispensing pharmaceutical and medical supply items from a dispensing unit comprising a cabinet having a processor and a plurality of retractable drawers, with at least some of the drawers having a plurality of receptacles for holding the items and with at least some of the drawers having lockable lids for at least some of the receptacles in the drawer, the method comprising:

entering user identification information into the processor to identify a user that is requesting access to the pharmaceutical or medical supply items held in the dispensing unit;

entering pharmaceutical or medical supply item identification information into the processor, the pharmaceutical or medical supply item identification information identifying specific pharmaceutical or medical supply items that the user requests to remove from the dispensing unit;

comparing the user identification information with an access list having information as to which of the requested pharmaceutical or medical supply items that the user may be given access based on the previously entered user identification information to determine one or more of the drawers to which the user may be given access;

unlocking one of the drawers having one of the requested pharmaceutical or medical supply items if the access list indicates that the user may have access to the requested pharmaceutical or medical supply item in that drawer;

retracting the unlocked drawer;

actuating a receptacle visual indicator adjacent one of the receptacles in the retracted drawer having the requested pharmaceutical or medical supply item;

unlocking the lid adjacent the actuated visual indicator if the retracted drawer includes at least some lockable lids to allow access to the receptacle adjacent the actuated visual indicator while preventing access to the other receptacles having lockable lids; and removing the requested pharmaceutical or medical supply item from the receptacle adjacent the actuated visual indicator.

2. A method as in claim 1, further comprising entering the quantity of each item to be removed into the dispensing unit.

3. A method as in claim 1, further comprising entering or selecting patient identification information into the dispensing unit.

4. A method as in claim 3, wherein the entering step comprises selecting patient identification information from a list stored in the dispensing unit.

5. A method as in claim 1, further comprising producing an alarm if access is attempted to one of the receptacles for which an adjacent receptacle visual indicator is not actuated.

6. A method as in claim 1, wherein all other drawers remain locked.

7. A method as in claim 2, wherein the removing step comprises at least partially removing a lid covering the receptacle and sensing removal of the lid.

8. A method as in claim 7, wherein the lid is locked prior to entering user and item identification.

9. A method as in claim 8, wherein the lid is unlocked upon actuation of the adjacent visual indicator.

10. A method as in claim 7, wherein sensing of lid removal is used to confirm access to the receptacle and to acknowledge removal of the initially entered quantity.

11. A method as in claim 7, further comprising producing an alarm if the lid is not replaced following removal of the item.

12. A method as in claim 2, further comprising touching an item button corresponding to the receptacle to confirm removal of the item and quantity.

13. A method as in claim 1, further comprising actuating a drawer visual indicator on the unlocked drawer.

14. A method as in claim 1, further comprising actuating a second receptacle visual indicator adjacent another receptacle in the retracted drawer having another item from the entered item identification information and removing an item from that receptacle.

15. A method as in claim 1, further comprising closing and locking the drawer if no receptacle visual indicators are actuated.

16. A method as in claim 15, further comprising unlocking a second one of the drawers having at least one item from the entered item identification information if the user may have access to that drawer, and retracting the unlocked drawer.

17. A method as in claim 2, wherein a plurality of the receptacles each contain multiple items of the same type.

18. A method as in claim 17, further comprising entering a quantity of more than one of the same type of item into the dispensing unit, and actuating a visual indicator adjacent a second receptacle if a first of the receptacles having the item lacks a sufficient quantity to fill the requested quantity.

19. A method as in claim 18, wherein each receptacle is covered by a lid and has a corresponding item button, and wherein the visual indicator adjacent the second receptacle is actuated after the lid for the first receptacle has been lifted and the corresponding item button selected.

20. A method as in claim 1, further comprising periodically restocking any emptied receptacles.

21. A method as in claim 20, wherein the restocking step comprises allowing access to only one receptacle at a time as the receptacles are refilled.

22. A method as in claim 20, wherein the restocking step comprises providing simultaneous access to all receptacles of a drawer when refilling the receptacles.

23. A method as in claim 20, further comprising entering a list of items and associated quantities that are to be restocked into the dispensing unit prior to restocking.

24. A method as in claim 23, wherein the entering step comprises electronically transferring the list of items and quantities from a remote processor.

25. A method as in claim 24, further comprising touching a touch-sensitive button adjacent one of the receptacles to be restocked after the receptacle has been restocked to confirm completion of restocking and that the initially entered quantity has actually been restocked.

26. A method as in claim 25, further comprising entering updated quantity information into the dispensing unit if the quantity to be restocked is different from the initially entered quantity.

27. A method as in claim 1, further comprising requiring witness identification information to be entered into the dispensing unit prior to allowing access to selected ones of the drawers.

28. A method for dispensing pharmaceutical or medical supply items from a dispensing unit comprising a cabinet having a processor and a plurality of retractable drawers, with at least some of the retractable drawers having a plurality receptacles for holding the items and with at least some of the receptacles including lids which cover the receptacles, the method comprising:

entering user identification information into the processor to identify a user that is requesting access to the pharmaceutical or medical supply items held in the dispensing unit;

entering pharmaceutical or medical supply item identification information into the processor, the pharmaceutical or medical supply item identification information identifying specific types of pharmaceutical or medical supply items that the user requests to remove from the dispensing unit;

entering the quantity of each type of pharmaceutical or medical supply item into the processor that the user wishes to remove from the dispensing unit;

actuating a receptacle visual indicator adjacent one of the receptacles having one of the requested types of pharmaceutical or medical supply items if the drawer has multiple receptacles;

manually moving the lid covering the receptacle adjacent the actuated visual indicator and sensing movement of the lid to produce a record that access to the receptacle was attempted; and removing the previously entered quantity of the requested pharmaceutical or medical supply item from the receptacle adjacent the actuated visual indicator.

29. A method as in claim 28, further comprising producing an alarm if one of the lids is moved that is not adjacent the receptacle having the actuated visual indicator.

30. A method as in claim 28, further comprising actuating a second receptacle visual indicator adjacent a second receptacle having another type of requested pharmaceutical or medical supply item after removal of the first type of pharmaceutical or medical supply item from the first receptacle.

31. A method as in claim 1, wherein each receptacle holds only a single item.

32. A method as in claim 28, wherein each receptacle holds only a single item.

33. A method as in claim 28, further comprising periodically restocking items into depleted receptacles.

34. A method as in claim 33, wherein the restocking step comprises simultaneously removing all lids from the drawer to gain access to the receptacles.

35. A method as in claim 23, further comprising manually entering a modified quantity of items to be restocked into the dispensing unit if the quantity of actual items to be restocked is less than the entered quantity 36. A method as in claim 33, further comprising entering a list of items and associated quantities that are to be restocked into the dispensing unit prior to restocking, and wherein the entering step comprises electronically transferring the list of items and quantities from a remote processor.

37. A method as in claim 28, wherein at least one of the lids is transparent to permit visual access.

38. A method as in claim 28, wherein at least some of the lids are opaque to prevent the user from gaining visual access to the items.

39. A method as in claim 1, wherein the lids are slidable held over each of the receptacles.

40. A method as in claim 1, wherein the lids are attached over each of the receptacles by a hinge.

41. A method as in claim 28, wherein the lids are slidable held over each of the receptacles.

42. A method as in claim 28, wherein the lids are attached over each of the receptacles by a hinge.

43. A method as in claim 28, wherein a plurality of the receptacles each contain multiple items of the same type, and further comprising entering a quantity of more than one of the same type of item into the dispensing unit, and actuating a visual indicator adjacent a second receptacle if a first of the receptacles having the item lacks a sufficient quantity to fill the requested quantity.

* * * * *